(12) United States Patent
Lundquist et al.

(10) Patent No.: US 6,241,702 B1
(45) Date of Patent: *Jun. 5, 2001

(54) RADIO FREQUENCY ABLATION DEVICE FOR TREATMENT OF THE PROSTATE

(75) Inventors: Ingemar H. Lundquist, Pebble Beach; Stuart D. Edwards, Los Altos; Hugh R. Sharkey, Redwood City; Ronald G. Lax; James A. Baker, Jr., both of Grass Valley; Phillip R. Sommer, Newark, all of CA (US)

(73) Assignee: Vidamed, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/094,255

(22) Filed: Jun. 9, 1998

Related U.S. Application Data

(63) Continuation of application No. 08/701,887, filed on Aug. 23, 1996, now Pat. No. 5,762,626, which is a continuation of application No. 08/191,258, filed on Feb. 2, 1994, now Pat. No. 5,549,644, which is a continuation-in-part of application No. 08/109,190, filed on Aug. 19, 1993, now Pat. No. 5,409,453, which is a continuation-in-part of application No. 08/061,647, filed on May 13, 1993, now Pat. No. 5,421,819, and a continuation-in-part of application No. 08/062,364, filed on May 13, 1993, now Pat. No. 5,435,805, which is a continuation-in-part of application No. 08/012,370, filed on Feb. 2, 1993, now Pat. No. 5,370,675, which is a continuation-in-part of application No. 07/929,638, filed on Aug. 12, 1992, now abandoned.

(51) Int. Cl.$^7$ ............................... A61B 17/20; A61F 2/00
(52) U.S. Cl. .............................. 604/22; 607/101
(58) Field of Search ................... 604/22, 21, 20; 606/33, 39, 41, 45; 607/101, 105, 99; 128/642, 736

(56) References Cited

U.S. PATENT DOCUMENTS

| 1,879,248 | 9/1932 | Honsaker . |
| 2,008,526 | 7/1935 | Wappler et al. . |

(List continued on next page.)

FOREIGN PATENT DOCUMENTS

| 2121675 | 5/1990 | (JP) . |
| 92/10142 | 6/1992 | (WO) . |

(List continued on next page.)

OTHER PUBLICATIONS

U.S. application No. 07/832,115, Makower et al., filed Feb. 6, 1992.*

(List continued on next page.)

*Primary Examiner*—Sharon Kennedy
(74) *Attorney, Agent, or Firm*—Flehr Hohbach Test Albritton & Herbert LLP

(57) ABSTRACT

A medical device for the treatment by radio frequency ablation of a target volume in tissue of a prostate comprising an elongate probe member having proximal and distal extremities and having a passage therein extending from the proximal extremity to the distal extremity. The elongate probe member is sized so that it can be introduced into the urethra. At least one guide tube having proximal and distal extremities is mounted in the passage of the elongate probe member for nonlongitudinal movement therein. The at least one guide tube has a lumen extending therethrough from the proximal extremity to the distal extremity. A radio frequency conductive electrode is disposed in the lumen. A handle is coupled to the proximal extremity of the elongate probe member and includes a finger actuatable mechanism secured to the radio frequency electrode for advancing and retracting the radio frequency electrode with respect to the at least one guide tube. The distal extremity of the at least one guide tube has a curved surface for directing the radio frequency electrode sidewise of the longitudinal axis into the tissue of the prostate.

15 Claims, 11 Drawing Sheets

U.S. PATENT DOCUMENTS

| | | |
|---|---|---|
| 2,038,393 | 4/1936 | Wappler . |
| 3,470,876 | 10/1969 | Barchilon . |
| 3,556,079 | 1/1971 | Omizo . |
| 3,595,239 | 7/1971 | Peterson . |
| 4,016,886 | 4/1977 | Doss et al. . |
| 4,119,102 | 10/1978 | LeVeen . |
| 4,204,549 | 5/1980 | Paglione . |
| 4,311,154 | 1/1982 | Sterzer et al. . |
| 4,402,311 | 9/1983 | Hattori . |
| 4,411,266 | 10/1983 | Cosman . |
| 4,448,198 | 5/1984 | Turner . |
| 4,470,407 | 9/1984 | Hussein . |
| 4,474,174 | 10/1984 | Petruzzi . |
| 4,524,770 | 6/1985 | Orandi . |
| 4,552,554 | 11/1985 | Gould et al. . |
| 4,565,200 | 1/1986 | Cosman . |
| 4,568,329 | 2/1986 | Mahorkar . |
| 4,682,596 | 7/1987 | Bales et al. . |
| 4,719,914 | 1/1988 | Johnson . |
| 4,800,899 | 1/1989 | Elliott . |
| 4,813,429 | 3/1989 | Eshel et al. . |
| 4,823,791 | 4/1989 | D'Amelio et al. . |
| 4,860,744 | 8/1989 | Johnson et al. . |
| 4,905,667 | 3/1990 | Foerster et al. . |
| 4,907,589 | 3/1990 | Cosman . |
| 4,919,129 | 4/1990 | Weber, Jr. et al. . |
| 4,943,290 | 7/1990 | Rexroth et al. . |
| 4,950,267 | 8/1990 | Ishihara et al. . |
| 5,007,908 | 4/1991 | Rydell . |
| 5,071,418 | 12/1991 | Rosenbaum . |
| 5,100,423 * | 3/1992 | Fearnot ................................ 604/22 |
| 5,122,137 | 6/1992 | Lennox . |
| 5,144,960 * | 9/1992 | Mehra et al. ........................ 128/786 |
| 5,197,963 | 3/1993 | Parins . |
| 5,234,004 | 8/1993 | Hascoet et al. . |
| 5,249,585 | 10/1993 | Turner et al. . |
| 5,261,400 * | 11/1993 | Bardy ....................................... 607/5 |
| 5,273,524 | 12/1993 | Fox et al. . |
| 5,334,183 * | 8/1994 | Wuchinich ............................ 606/46 |
| 5,370,675 * | 12/1994 | Edwards et al. ..................... 607/101 |
| 5,409,453 * | 4/1995 | Lundquist et al. ..................... 604/22 |
| 5,421,819 * | 6/1995 | Edwards et al. ........................ 604/22 |
| 5,435,805 * | 7/1995 | Edwards et al. ........................ 604/22 |
| 5,549,644 * | 8/1996 | Lundquist et al. ..................... 604/22 |
| 5,762,626 * | 6/1998 | Lundquist et al. ..................... 604/22 |

FOREIGN PATENT DOCUMENTS

| | | |
|---|---|---|
| 93/15664 | 8/1993 | (WO) . |
| 9315664 * | 8/1993 | (WO) . |

OTHER PUBLICATIONS

Greenwald Surgical Company, Inc., "Orandi Resectoscope Injection Needle for Injection of Local Anesthetics," (Undated) Sheet No. P000121.

E.F. Nation, M.D., "Evolution of Knife–Punch Resectoscope," (Apr. 1976) Urology, vol. VII, No. 4, pp. 417–427.

R. Gutierrez, "Transurethral Treatment of Bladder Neck Obstructions: Endoscopic Prostatic Resection," (Apr. 1933) History of Urology, vol. II, Chapter V, pp. 137–186.

C.W. Ogden, Heat and the Prostate from Electrolysis to Microwaves: Lessons from an Historical Perspective, (Undated) Abstract, 2 sheets, p. 366.

Graversen, et al., "Transurethral incisions of the prostate under local anaesthesia in high–risk patients: a pilot study," (1987) Abstract, HealthGate Home Page, p. P000115.

Miller, et al., "Integrated cystoscope: first rigid multipurpose operating cystoscope for local anesthetic endoscopy," (1989) Abstract, HealthGate Home Page, p. P000116.

Orandi, "Urological endoscopic surgery under local anesthesia: a cost–reducing idea," (1984) Abstract, HealthGate Home Page, p. P000117.

Orandi, "Transurethral resection versus transurethral incision of the prostate," (1990) Abstract, HealthGate Home Page, p. P000118.

H. LeVeen, "Method for treating benign and malignant tumors utilizing radio frequency," (Nov. 16, 1976) Abstract, USPTO.gov, U.S. Patent No. 3,991,770, pp. P000119–P000120.

R. Auhll, "The Use of the Resectoscope in Gynecology," (Oct. 1990) Biomedical Business International, pp. 91–99.

L. Geddes, "A Short History of the Electrical Stimulation of Excitable Tissue Including Electrotherapeutic Applicaitons," (1984) A Supplement to The Physiologist, vol. 27, No. 1, pp. P000066–P000071.

W. Moseley, M.D., "The History of Treatment of BPH Including Current Treatment Alternatives," (Undated) pp. P000187–P000190.

D. Paulson, M.D., "Diseases of the Prostate," (1989) Clinical Symposia, vol. 41, No. 2., pp. P000191–P000195.

T. Kirwin, "The Treatment of Prostatic Hypertrophy by a New 'Shrinkage' Method," (Aug. 1934) J. Urology, pp. 481–494.

* cited by examiner

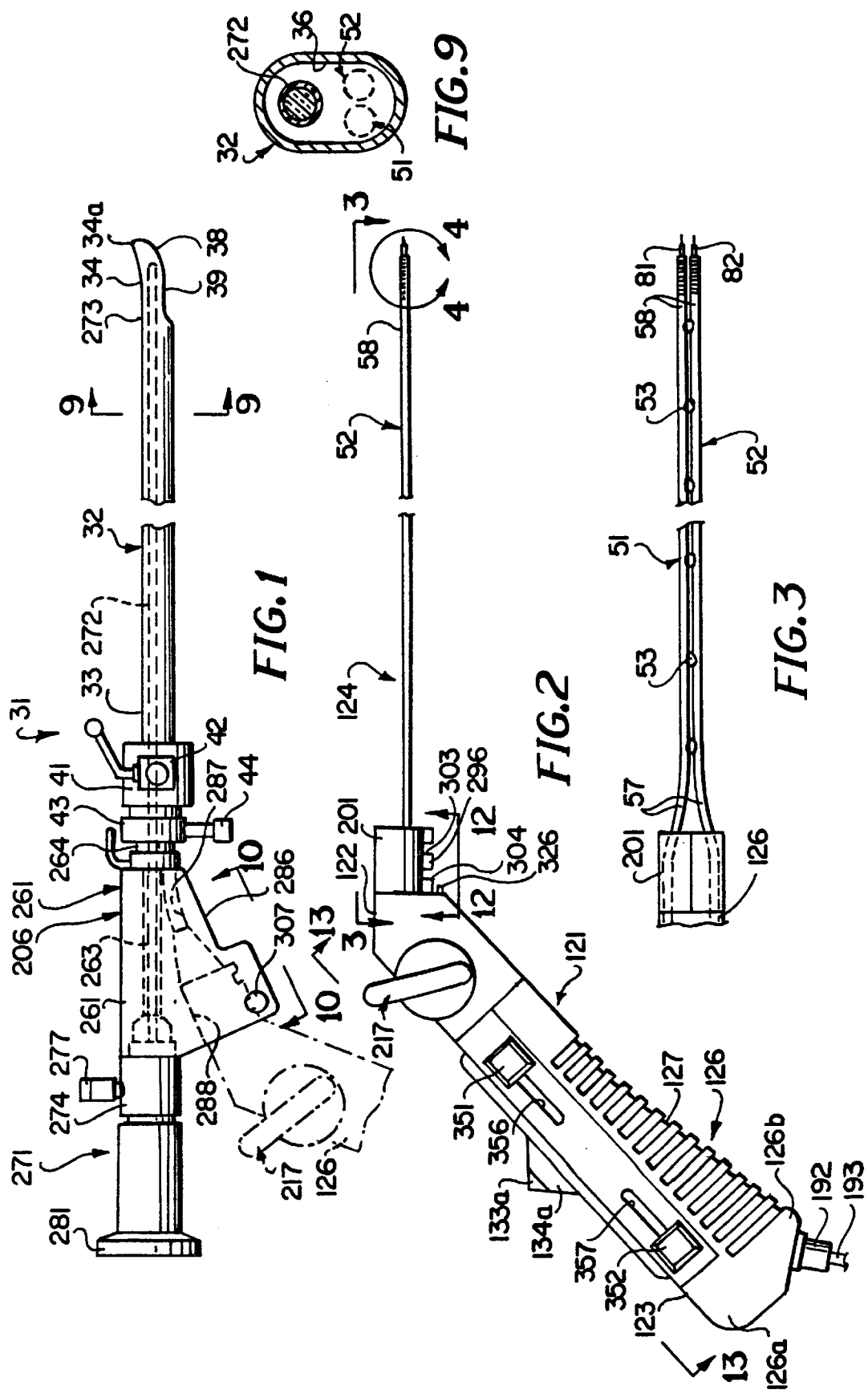

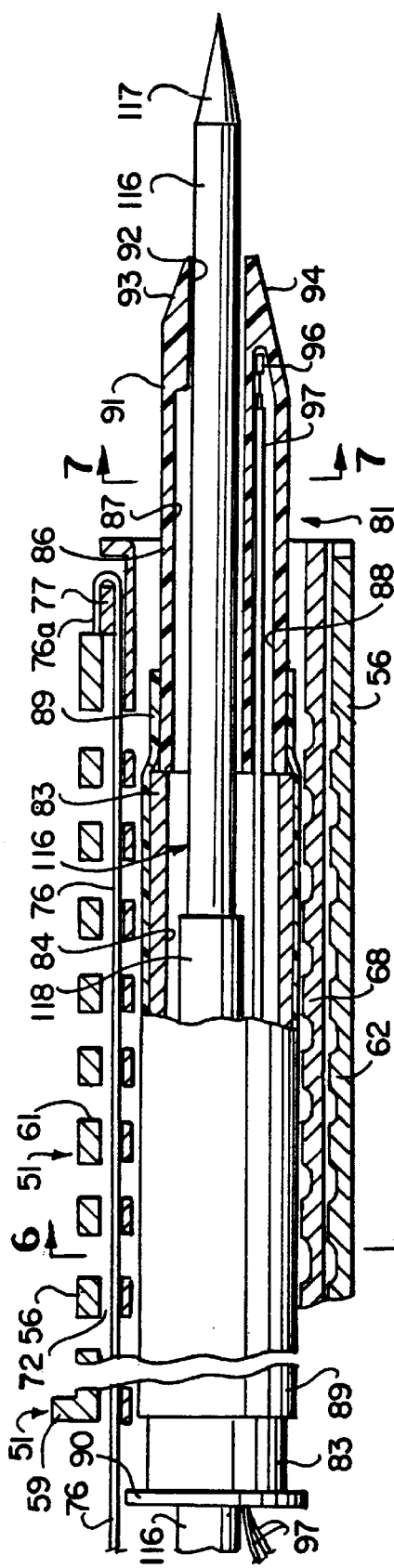
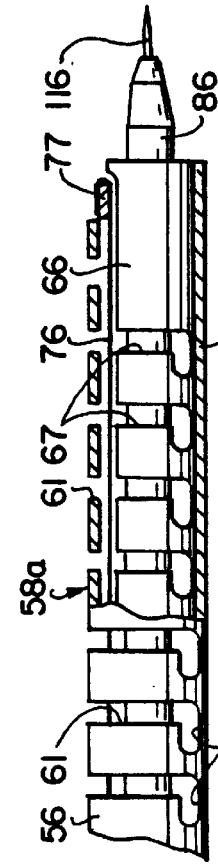
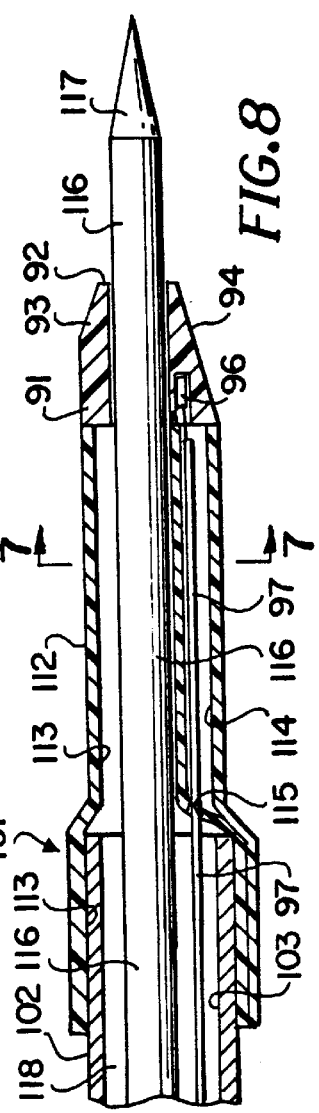
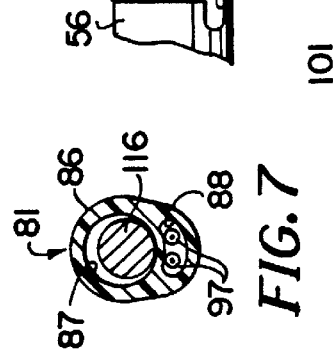
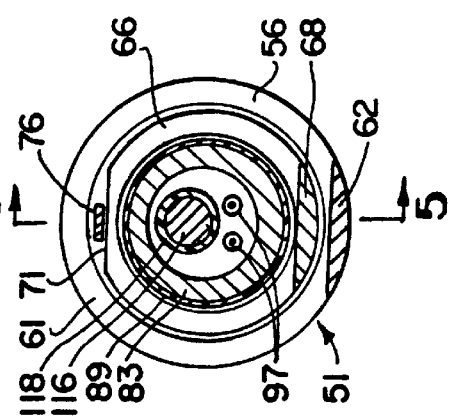

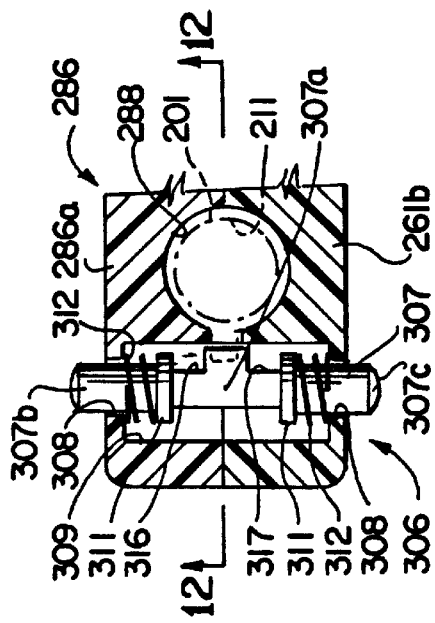
FIG.10
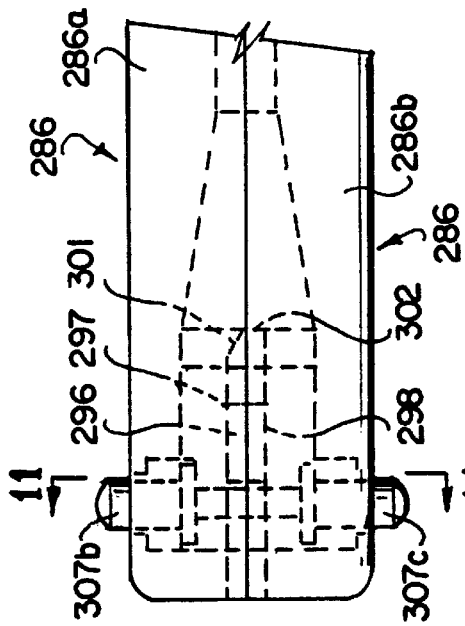
FIG.11
FIG.12
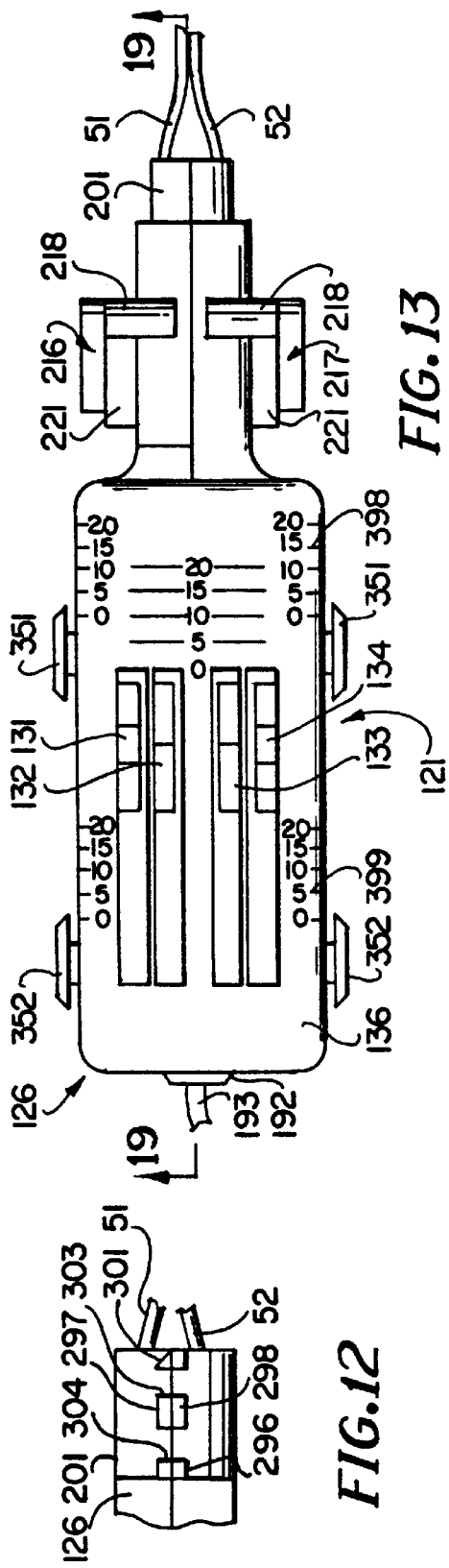
FIG.13

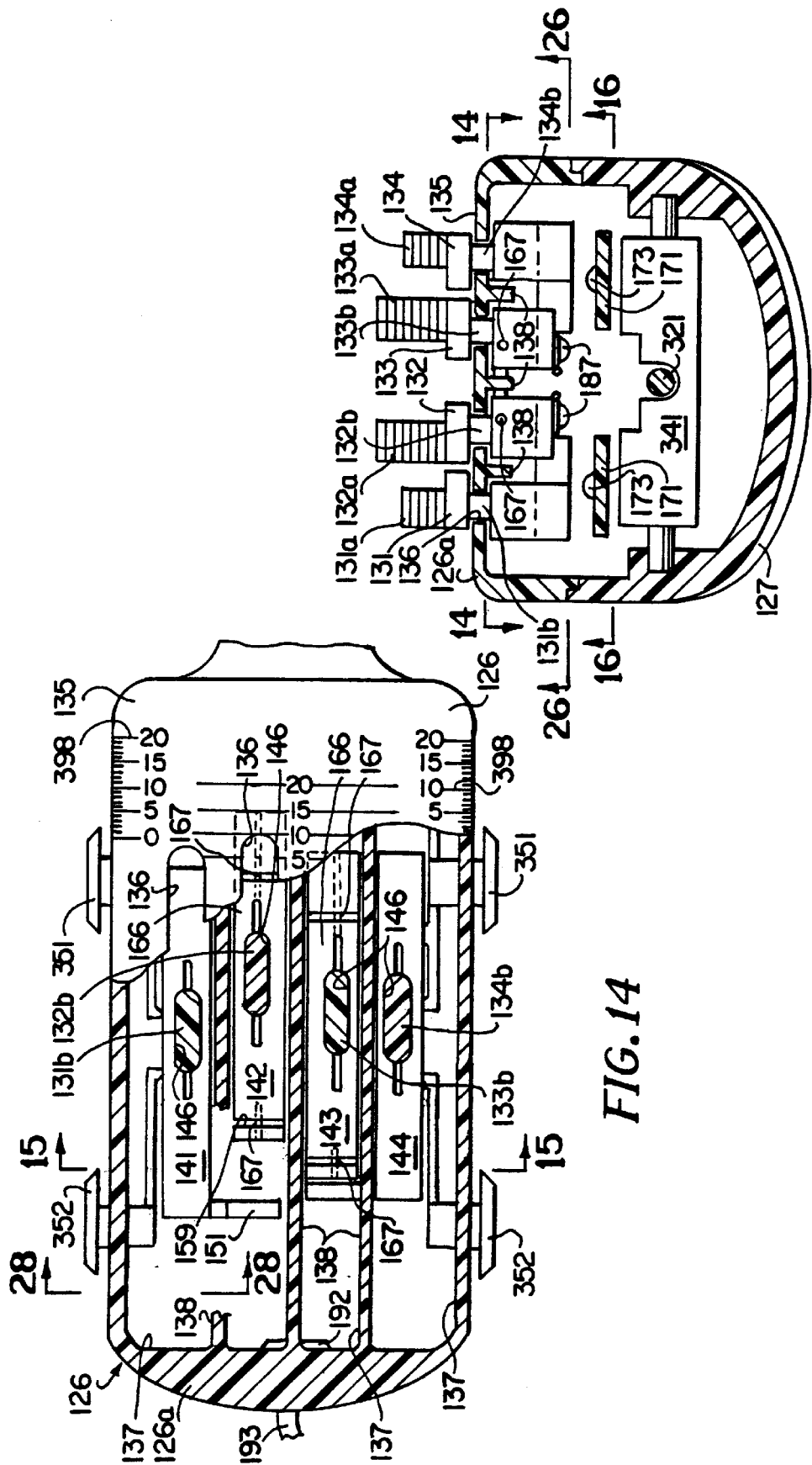

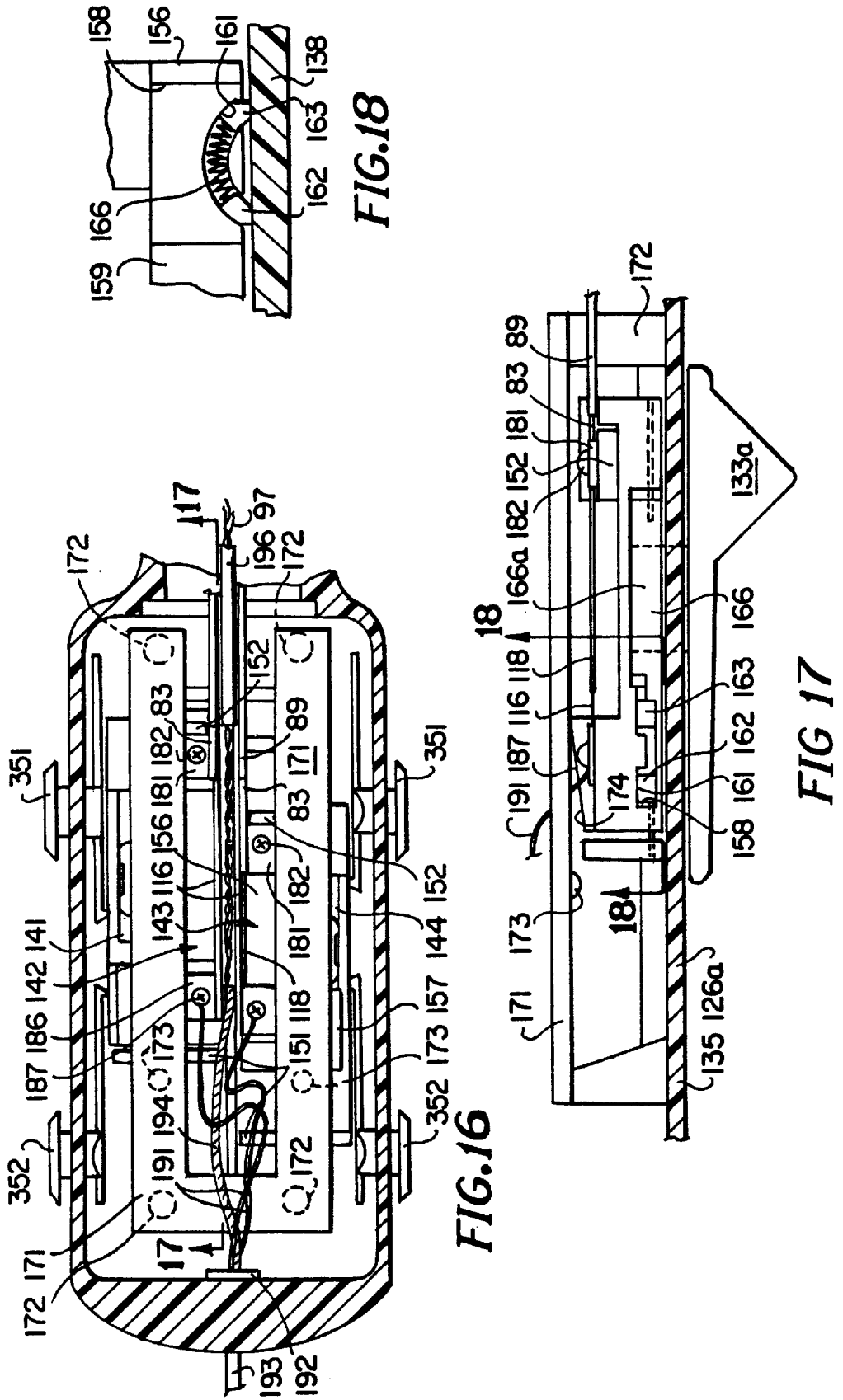

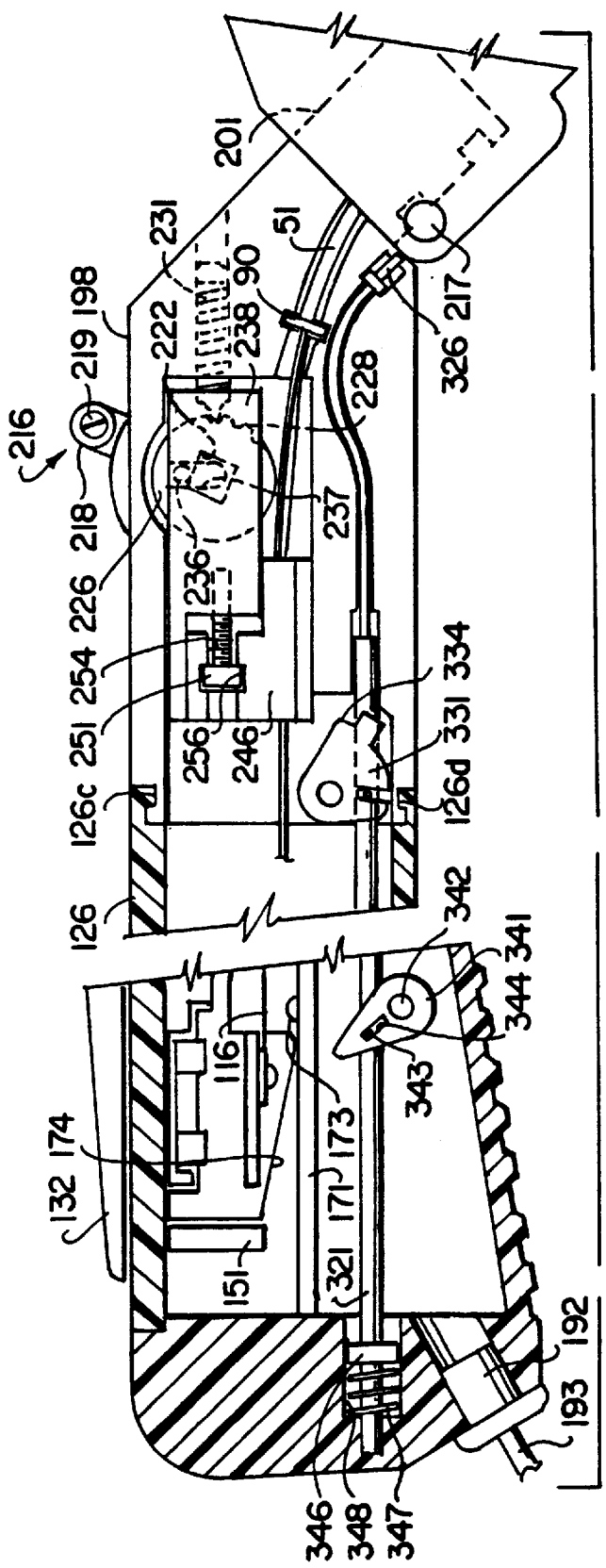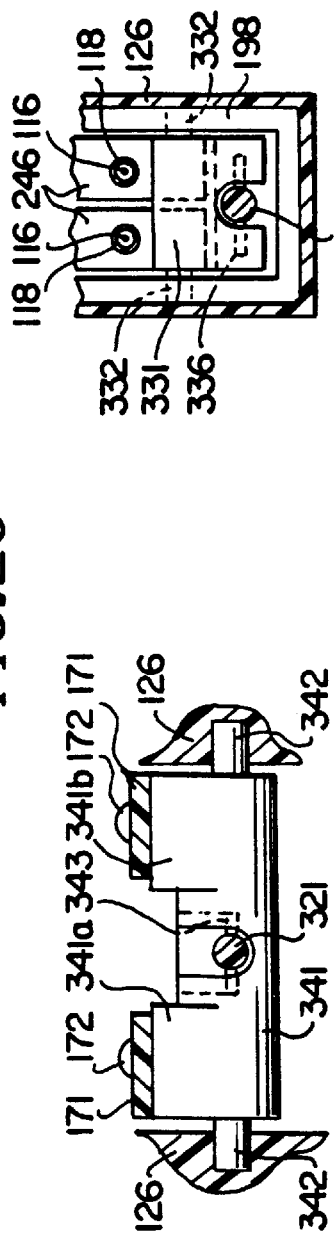
*FIG.20*
*FIG.22*
*FIG.21*

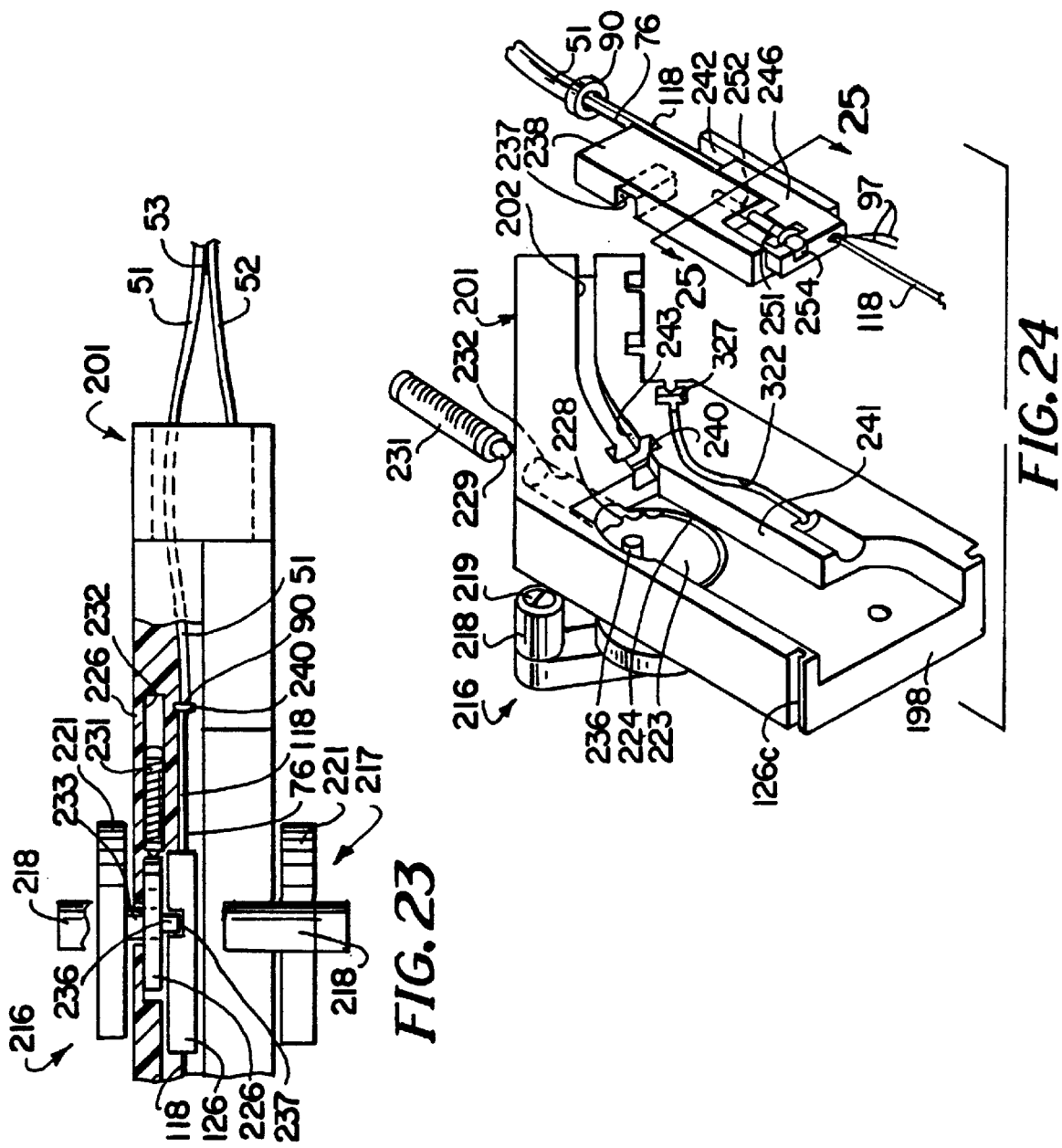

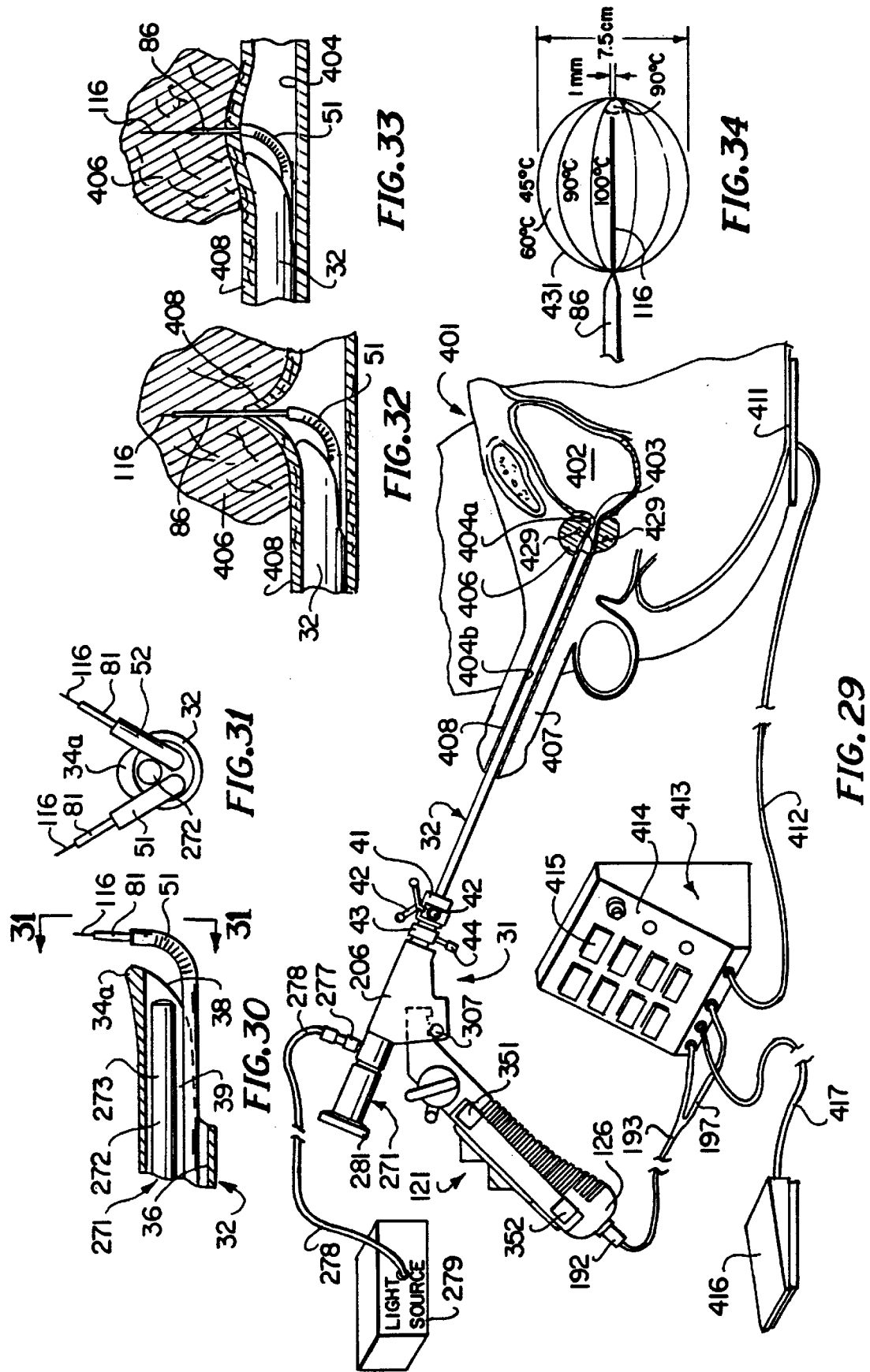

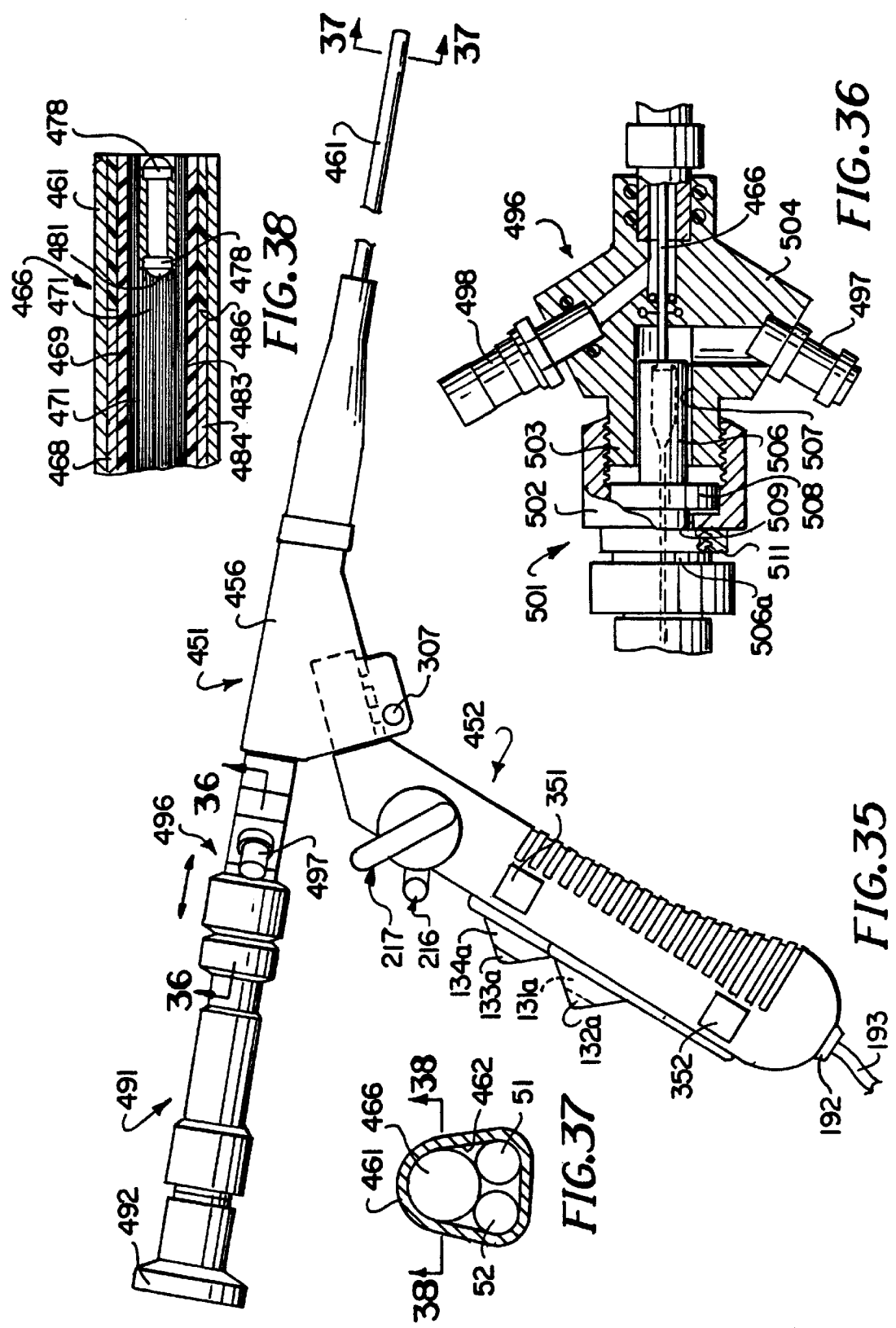

RADIO FREQUENCY ABLATION DEVICE FOR TREATMENT OF THE PROSTATE

This is a continuation of application Ser. No. 08/701,887 filed Aug. 23, 1996, now U.S. Pat. No. 5,762,626, which is a continuation of application Ser. No. 08/191,258 filed Feb. 2, 1994, now U.S. Pat. No. 5,549,644, which is a continuation-in-part of application Ser. No. 08/109,190, filed Aug. 19, 1993, now U.S. Pat. No. 5,409,453, which is a continuation-in-part of application Ser. No. 08/061,647 filed May 13, 1993, now U.S. Pat. No. 5,421,819, and a continuation-in-part of application Ser. No. 08/062,364 filed May 13, 1993, now U.S. Pat. No. 5,435,805, which is a continuation-in-part of application Ser. No. 08/012,370 filed Feb. 2, 1993, now U.S. Pat. No. 5,370,675, which is a continuation-in-part of application Ser. No. 07/929,638 filed Aug. 12, 1992, abandoned.

This invention relates to a transurethral needle ablation device with cystoscope and method for the treatment of conditions of the prostate in human males.

Benign prostatic hypertrophy or hyperplasia (BPH) is a common medical problem associated with aging men. Surgical procedures heretofore utilized to correct this problem have been expensive, time consuming and painful. In addition, such surgical procedures can have many undesirable side effects. There is therefore a need for a device and method which overcomes theme disadvantages.

In general, it is an object of the present invention to provide a transurethral needle ablation device with cystoscope and method which can be utilized for the treatment of conditions of the prostate of the human male and particularly BPH.

Another object of the invention is to provide a device and method of the above-character which utilizes radio frequency energy.

Another object of the invention is to provide a device and method of the above-character in which the urethral wall is protected from radio frequency energy during ablation.

Another object of the invention is to provide a device and method of the above-character in which the needle electrode cannot penetrate the insulating sleeve.

Another object of the invention is to provide a device and method of the above-character in which controls are provided to prevent undesired destruction of tissue.

Another object of the invention is to provide a device and method of the above-character in which many safety features are provided.

Another object of the invention is to provide a device of the above-character in which the insulating sleeve can be withdrawn without displacing the location of the needle electrode.

Another object of the invention is to provide a device and method of the above-character in which tenting of the urethral wall is minimized.

Another object of the invention is to provide a device and method of the above-character in which the length of the needle electrode exposed within the prostate and the positioning of the insulating sleeve with respect to the needle electrode can be preset before the device is introduced into the patient.

Another object of the invention is to provide a device and method of the above-character in which a brake mechanism in provided to retain the needle electrode in position when the insulating sleeve is being retracted.

Another object of the invention is to provide a device and method which can be readily utilized by the physician performing the procedure.

Another object of the invention is to provide a device and method of the above-character which permits the use of conventional cystoscopes.

Another object of the invention is to provide a device and method of the above-character in which an integral cystoscope is provided.

Another object of the invention is to provide a device and method of the above-character which is minimally invasive, efficacious and low in cost.

Another object of the invention is to provide a device and method of the above-character which can be utilized for selectively ablating prostatic tissue.

Another object of the invention is to provide a device and method of the above-character which sakes it possible to deliver low level radio frequency power directly to a very localized area of the prostate.

Another object of the invention is to provide a device and method of the above-character in which the device can be positioned by the use of transrectal ultrasound or direct vision.

Another object of the invention is to provide a device and method of the above-character in which safety is assured by monitoring urethral temperatures.

Another object of the invention is to provide a device of the above-character in which large lesions of extensive coagulative necrosis can be achieved.

Another object of the invention is to provide a device and method of the above-character in which patients can be treated without the use of anesthesia except for possibly a local anesthetic.

Another object of the invention is to provide a device and method in which the needle electrode can be introduced at substantially right angles to the longitudinal axis of the catheter and be caused to penetrate the urethral wall and extend directly into the prostatic tissue.

Another object of the invention is to provide a device and method of the above-character in which at least two lesions can be formed substantially simultaneously in the prostatic tissue.

Another object of the invention is to provide a device and method of the above-character in which the needle electrodes can be redeployed readily to create additional lesions in the same prostate.

Another object of the invention is to provide a device and method of the above-character in which the ablation to form lesions can be performed with great precision.

Additional objects and features of the invention will appear from the following description in which the preferred embodiments are set forth in conjunction with the accompanying drawings.

FIG. 1 is a side-elevational view of a bridge with an attached sheath having a conventional cystoscope mounted therein.

FIG. 2 is a side-elevational view of a handle and guide tube assembly for use with the bridge and sheath with a conventional cystoscope as shown in FIG. 1 to provide a transurethral ablation device incorporating the present invention.

FIG. 3 is a top-elevational view looking along the line 3—3 of FIG. 2.

FIG. 4 is an enlarged view partly in cross section of the distal extremity of the guide tube assembly shown in FIG. 2 and encircled by the arrows 4—4.

FIG. 5 is an enlarged detail view partially in cross section of the distal extremity of the guide tube assembly taken along the line 5—5 of FIG. 6.

FIG. 6 is a cross-sectional view taken along the line 6—6 of FIG. 5.

FIG. 7 is a cross-sectional view taken along the line 7—7 of FIGS. 5 and 8.

FIG. 8 is a partial cross-sectional view of the distal extremity of another embodiment of a guide tube assembly incorporating the present invention.

FIG. 9 is a cross-sectional view taken along the line 9—9 of FIG. 1.

FIG. 10 is a view looking along the line 10—10 of FIG. 1.

FIG. 11 is a cross-sectional view taken along the line 11—11 of FIG. 10.

FIG. 12 is a view looking along the line 12—12 of FIG. 3.

FIG. 13 is a view looking along the line 13—13 of FIG. 2.

FIG. 14 is an enlarged view similar to FIG. 13 and taken along the line 14—14 of FIG. 15 with certain portions being broken away.

FIG. 15 is a cross-sectional view taken along the line 15—15 of FIG. 14.

FIG. 16 is a cross-sectional view taken along the line 16—16 of FIG. 15.

FIG. 17 is a cross-sectional view taken along the line 17—17 of FIG. 16.

FIG. 18 is a cross-sectional view taken along the line 18—18 of FIG. 17.

FIG. 20 is a cross-sectional view similar to FIG. 19 but showing the safety mechanism in disengaged positions.

FIG. 21 is a cross-sectional view taken along the line 21—21 of FIG. 19.

FIG. 22 is a cross-sectional view taken along the line 22—22 of FIG. 19.

FIG. 23 is a view looking along the line 23—23 of FIG. 19.

FIG. 24 is an exploded isometric view of the mechanism as shown in FIG. 23.

FIG. 25 is a cross-sectional view taken along the line 25—25 of FIG. 24.

FIG. 29 is a schematic illustration showing the manner in which the transurethral needle ablation device is utilized in performing an ablation procedure.

FIG. 30 is an enlarged cross-sectional view of the distal extremity of the transurethral needle ablation device showing the deployment of the needle electrodes during the ablation procedure.

FIG. 31 is a view looking along the line 31—31 of FIG. 30.

FIG. 32 is an enlarged cross-sectional view showing one of the needle electrodes penetrating the urethral wall and creating a tenting effect.

FIG. 33 is a cross-sectional view similar to FIG. 32 but showing the retraction of the insulation sheath with respect to the needle electrode and the elimination of the tenting in the urethral wall.

FIG. 34 is a thermal gradient map showing the temperatures which occur in the tissue of the prostate during an ablation procedure.

FIG. 35 is a cross-sectional view of another embodiment of a transurethral needle ablation device incorporating the present invention.

FIG. 36 is a cross-sectional view taken along the line 36—36 of FIG. 35.

FIG. 37 is a cross-sectional view taken along the line 37—37 of FIG. 35.

FIG. 38 is a cross-sectional view taken along the line 38—38 of FIG. 37.

Figure 19:
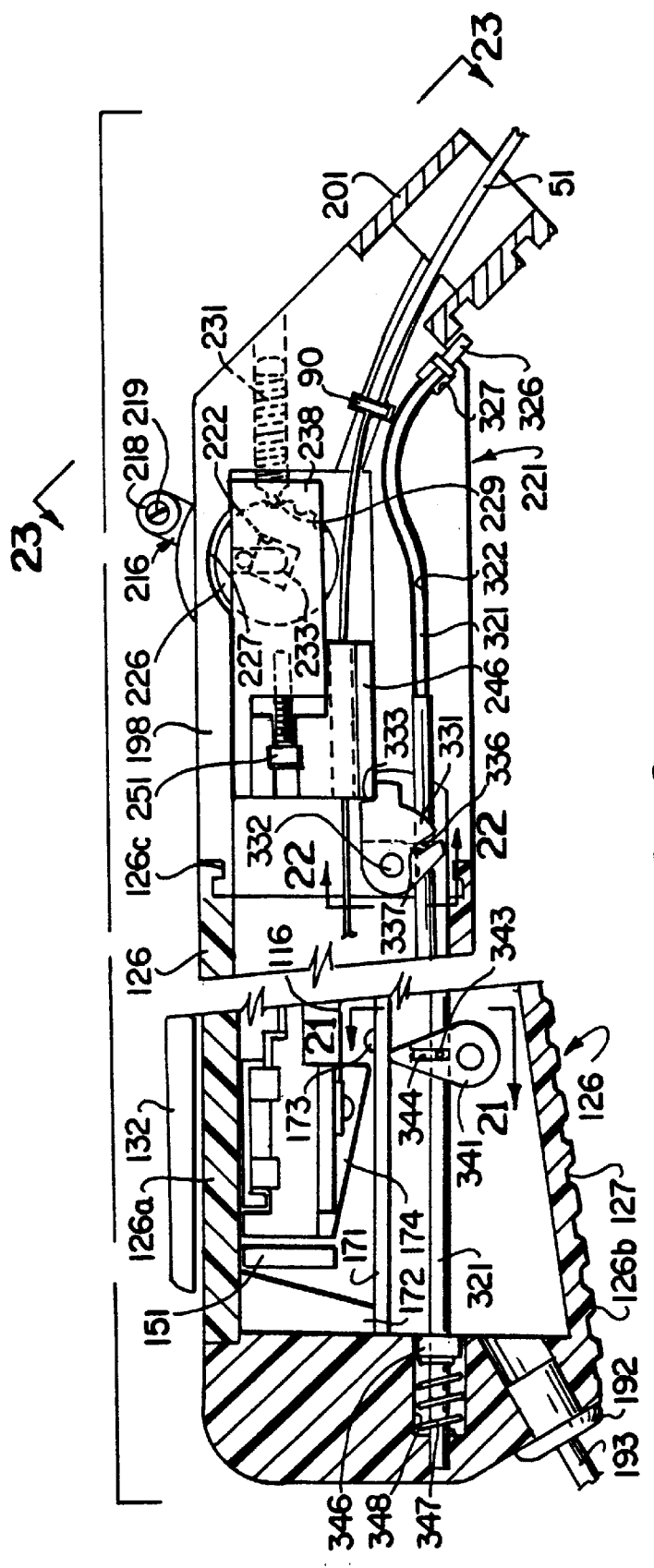
FIG. 19 is a cross-sectional view of the handle assembly taken along the line 19—19 of FIG. 13 and showing safety mechanisms in operative positions.

In general, the transurethral needle ablation device is for the treatment of the prostate of a human male utilizing radio frequency energy from a radio frequency power source in which the human male has a bladder with a base, a prostate, and a penis with a urethra therein formed by a urethral wall extending from the base of the bladder through the prostate and the penis along a longitudinal axis with the prostate having prostatic tissue surrounding the urethral wall. The device comprises a sheath having proximal and distal extremities and having a lumen extending from the proximal to the distal extremity. A guide tube assembly is slidably mounted in the lumen in the sheath and has proximal and distal extremities and a longitudinal axis. A needle electrode is slidably mounted in the lumen in the guide tube assembly and has proximal and distal extremities. An insulating sleeve is disposed about the needle electrode within the lumen of the guide tube assembly and has proximal and distal extremities with the distal extremity of the insulating sleeve being positioned so that the distal extremity of the needle electrode is exposed. Handle means is provided forming a handle adapted to be grasped by the human hand. Means forming a bridge is secured to the handle means and to the proximal extremity of the sheath for connecting the handle means to the proximal extremity of the sheath. Means is carried by the handle means and the bridge means and coupled to the guide tube assembly for moving the distal extremity of the guide tube assembly from a retracted position within the distal extremity of the sheath and an extended position distally of the distal extremity of the sheath. Means is carried by the handle means and coupled to the guide tube assembly for causing bending of the distal extremity of the guide tube assembly at an angle with respect to its longitudinal axis whereby the lumen in the guide tube assembly can be directed so it faces toward the urethral wall. Means is carried by the handle means and coupled to the needle electrode and the insulating sleeve for advancing and retracting the needle electrode with respect to the guide tube assembly and means adapted to couple the needle electrode to the radio frequency power source whereby when the sheath is positioned in the urethra with its distal extremity in the vicinity of the prostate, the needle electrode can be advanced through the urethral wall and into the tissue of the prostate to permit the application of radio frequency energy from the radio frequency power source to the needle electrode to cause the formation of a lesion in the tissue of the prostate.

In the method of the present invention for the treatment of benign prostatic hyperplasia of the prostate of the human male having a bladder with a base, a prostate and a penis with a urethra therein formed by a urethral wall extending from the base of the bladder through the prostate and the penis along a longitudinal axis with the prostate having tissue surrounding the urethral wall by the use of a needle electrode comprising the steps of introducing the needle electrode into the urethra and advancing it longitudinally of the urethra along the longitudinal axis until the needle electrode is in the vicinity of the prostate. The needle electrode is then advanced in a direction at a substantial angle to the longitudinal axis of the urethra to penetrate the urethral wall and to extend into the tissue of the prostate. Radio frequency energy is applied to the needle electrode at a sufficient power level and for a sufficient period of time to raise the temperature of the tissue in the prostate in the vicinity of the needle electrode to cause the formation of a lesion in the prostatic tissue.

Figure 26:
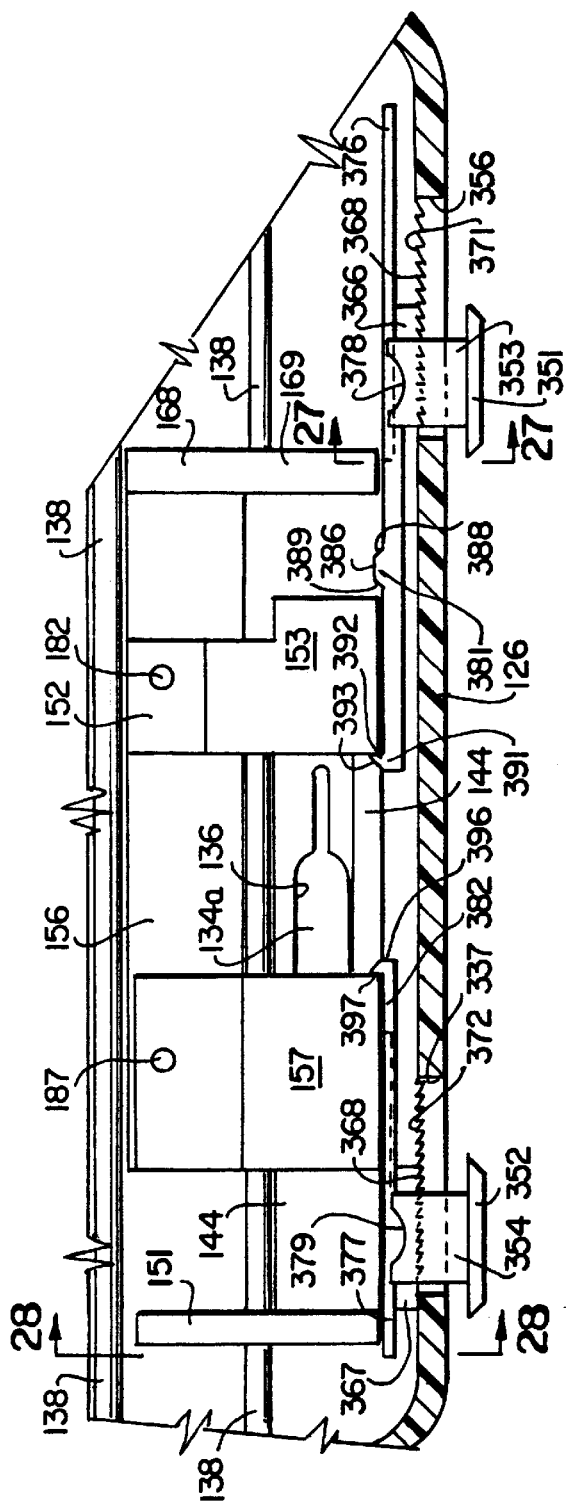
FIG. 26 is a partial cross-sectional view taken along the line 26—26 of FIG. 15.
Figure 27:
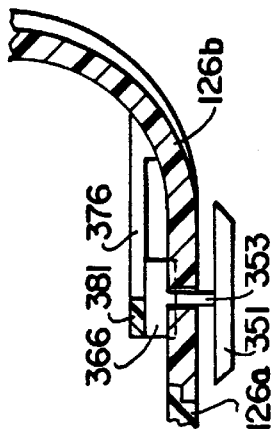
FIG. 27 is a cross-sectional view taken along the line 27—27 of FIG. 26.
Figure 28:
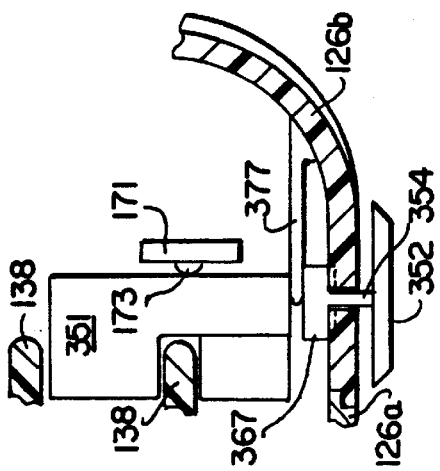
FIG. 28 is a cross-sectional view taken along the line 28—28 of FIG. 26.

More in particular, as shown in FIGS. 1–31 of the drawings, the transurethral needle ablation device 31 which can be identified as the TUNA III consists of a rigid sheath 32 which can be of a suitable type and size, as for example it can be in the form of a 22 French catheter-like delivery device having a length of 25 centimeters. The sheath 32 can be formed of a suitable material such as stainless steel and is provided with proximal and distal extremities 33 and 34 and has a lumen 36 (see FIG. 9) extending from the proximal extremity to the distal extremity. As shown particularly in FIG. 1, the distal extremity 34 has a forwardly and upwardly extending curved surface 38 through which an inclined opening 39 extends (see FIG. 30). The distal extremity 34 is also provided with a portion 34a of increased thickness to provide a blunt end for the sheath 32 to adapt it to enter into the urethra in the prostate during an ablation procedure hereinafter described.

The sheath 32 is provided with a hub 41 mounted on the proximal extremity 33 thereof. The hub 41 is provided with petcocks 42 on opposite sides of the hub. A locking ring 43 is rotatably mounted on the hub 41 and is provided with a handle 44 which is adapted to be utilized for mounting the proximal end 33 of the sheath 32 as hereinafter described.

First and second guide tube assemblies 51 and 52 are slidably mounted in the lumen 36 of the sheath 32. The guide tube assemblies 51 and 52 are substantially identical to each other and as shown are mounted side-by-side in the lumen 36 and fastened together by suitable means as solder 53.

A cross-sectional view of the guide tube assembly 51 is shown in FIG. 6. As shown therein it and similarly the guide tube assembly 52 consists of an outer guide tube 56 formed of a suitable material as stainless steel having a 15 gauge wall thickness with an outside diameter of 0.072" and an inside diameter of 0.060". The outer guide tube 56 is provided with proximal and distal extremities 57 and 58. The proximal extremity 57 is provided with a flange 59. A plurality of longitudinally spaced-apart circumferentially-extending L-shaped slots 61 are provided in the distalmost extremity of the distal extremity 58 of the outer guide tube 56, as for example the last 1.5 centimeters. The slots 61 subtend less than 360° and have a suitable width, as for example 0.012" and are spaced-apart a suitable distance, as for example 0.033". The slots 61 are L-shaped and are provided with a toe or short leg portion 61a having a length of 0.010". The slots 61 are not offset radially and therefore provide a backbone or rib 62 extending longitudinally of the outer guide tube 56. The outer guide tube 56 has a suitable length, as for example 14" with the slots 61 being formed in the distalmost portion 58a of 0.5". An inner guide tube 66 is disposed within the distal extremity 58 of outer guide tube 56 and has a suitable length, as for example 0.7". It is also formed of stainless steel of a suitable gauge, as for example 17 gauge and has an outside diameter of 0.059" and an inside diameter of 0.041". A plurality of longitudinally spaced circumferentially-extending I-shaped slots 67 are provided in the inner guide tube 66 and have the same dimensions as the slots 61 in the outer guide tube 56. The slots 67 are longitudinally aligned with the slots 61. The slots 67 are also axially aligned so that the backbone 68 is aligned with the backbone 62 (see FIG. 6). The inner guide tube 66 is provided with a flat 71 on its outer surface extending the length thereof. With the inner guide tube 66 disposed within the outer guide tube 56 a space 72 segment-shaped in cross section is formed between the inner surface of the outer guide tube 56 and the flat 71 (see FIG. 6) to provide space for a pull ribbon 76 which has a distal extremity 76a overlapping a cross member 77 secured within the distal extremity 58 of the outer guide tube 56 (see FIG. 5). The pull ribbon 76 extends interiorly of the outer guide 56 to the proximal extremity 57 of the guide tube assembly 51. The guide tube assemblies 51 and 52 as described above utilize a construction which is disclosed in co-pending application, Ser. No. 08/174,791, filed Dec. 29, 1993.

Insulation tube assemblies 81 and 82 are slidably mounted in the guide tube assemblies 51 and 52. The two assemblies 81 and 82 are substantially identical. Insulation tube assembly 81 consists of a tube 83 formed of a suitable material such as stainless steel of 19 gauge thin wall tubing often called hypotube which has an outside diameter of 0.043" and an inside diameter of 0.033". Tube 83 is provided with a large bore 84 (see FIGS. 5 and 6). A sleeve or sheath 86 of a suitably insulating material such as NYLON 11 abuts the distal extremity of the stainless steel tube 83 and is provided with a large lumen 87 and a smaller lumen 88 which open into the large lumen 84 of tube 83. The sleeve or sheath 86 is secured to the tube 83 in a suitable manner such as by an adhesive (not shown) and a shrink tube 89 that extends over the proximal extremity of the sleeve or sheath 86 and almost the entire length of tube 83 in close proximity, i.e. within 0.25" to a radially extending flange 90 of the tube 83. A tip 91 of formed insulation such as NYLON 11 is formed by the application of heat to the distal extremity of the sheath 86. It is provided with a bore 92 therein which is in registration with the lumen 87. The tip 91 is provided with a conically tapered surface 93 extending inwardly and forwardly toward the distal extremity with the taper 93 extending forwardly approximately less than one-half the total length of the tip 91 over 240° of the circumference. A more gradual taper 94 of approximately 15° from the horizontal is provided on the other 120° of circumference and extends the length of the tip 91 as shown in FIG. 5.

A thermocouple 96 is embedded within the tip 91 and is connected to insulated conductors 97 which extend through the bore 88 in sheath 86 and bore 84 of tube 83.

In order to prevent creeping during bending of the distal extremity of the insulating tube assembly 81, the interior of the shrink tubing 89 is adhesively bonded to the stainless steel tube 83 and also to the exterior of the insulating sleeve or sheath 86.

Another embodiment of an insulation sleeve assembly which can be substituted for assemblies 81 and 82 is shown in FIGS. 7 and 8. The insulation tube assembly 101 shown therein consists of a hypotube 102 similar to the tube 83 hereinbefore described and is provided with a lumen 103 extending therethrough. An insulation tube 112 is fitted over the distal extremity of the hypotube 102 and has a lumen 113 therein which is adapted to accommodate the distal extremity of the hypotube 102. The distal extremity of the insulation tube 112 is provided with an additional lumen 114 in which there is provided a mandrel (not shown) of a sufficient size to accommodate the two conductors 97 for the thermocouple 96. Similarly, another mandrel is provided in the lumen 113 distal of the hypotube 102 to provide a bore of a suitable size, as for example 0.018". With the mandrels therein and with the proximal extremity clamped to the distal extremity of the hypotube 102, the insulation tube 112 is stretched under low heat to approximately 150% of its original length. Thereafter the mandrels are removed. The thermocouple 96 may be mounted in the lumen 114 and the end sealed in an appropriate manner such as by a heat seal.

The conductors 97 from the thermocouple extend proximally in the bore 114 through a hole 115 (see FIG. 8) provided in insulation tube 112 so that the thermocouple conductors 97 can enter into the bore 103 of the hypotube 102. It has been found that this stretching of the insulation tube 112 is desirable because the stretching orients the plastic resin which is utilized in the insulation tube. Thus, the insulation tube has a higher flex modulus and a higher tensile yield strength. This stretching also increases the temperature resistance of the tube 112 by almost 30° C. In addition, the stretching sizes down the insulating tube so it fits well over the end of the stainless steel hypotube 101. By utilizing such a construction, it is possible to eliminate the use of the shrink tubing 89 in the prior embodiment.

A needle electrode 116 is slidably mounted in the lumen 84 of the insulation tube 83 and extends through the bore 92 of the tip 91. The needle electrode 116 is formed of a suitable material such as a nickel titanium alloy having superelastic properties so that it will return to its original configuration after being bent as hereinafter described. It is provided with a sharpened point 117 which is adapted to readily penetrate tissue. The needle electrode 116 has a suitable diameter, as for example slightly less than the bore 87 and the bore 92, as for example a diameter of 0.017".

The transurethral needle ablation device 31 (see FIG. 1) also includes handle means in the form of a handle 121 which is sized so it is adapted to fit into an adult human hand. The handle 121 is provided with proximal and distal or forward and rear extremities 122 and 123. Means is provided for connecting the proximal extremities of the guide tube assemblies 51 and 52 as well as the insulating sleeve assemblies 81 and 82 and the handle 121 to provide a handle and guide tube assembly 124 as shown in FIG. 2 as. hereinafter described. The bottom part 126b of the housing 126 is provided with transversely extending longitudinally spaced-apart serrations 127 facilitating the retention of the housing 126 by the hand.

The handle 121 consists of a housing 126 formed in an upper part 126a and a lower part 126b (see FIG. 15). The housing 126 is formed of a suitable plastic such as a. polycarbonate. Four slide control members 131, 132, 133, and 134 counting from left to right are slidably mounted on the top surface 135 of the housing 126 (see FIGS. 13 and 15) and are spaced transversely of the surface 135 and adapted to be moved longitudinally of the surface 135. In order to distinguish the slide control members from each other, the slide control members can be color coded and can be shaped differently for tactile feel. Thus they can be provided with upstanding protrusions in which the outside slide control members 131 and 134 are provided with upstanding truncated triangular portions 131a and 134a, respectively. Similarly, the slide control members 132 and 133 have upstanding portions 132a and 133a which are triangular. By way of example for color coding, the two outside slide control members 131 and 134 can be colored blue whereas the inside control members 132 and 133 can be colored grey.

The two outer slide control members 131 and 134 can be utilized for controlling the movement of the insulating sleeve assemblies 81 and 82 and similarly, the slide control members 132 and 133 can be utilized for controlling the movement of the needle electrodes 116. The slide control members 131–134 are provided with inwardly extending protruding portions 131b, 132b, 133b, and 134b (see FIG. 14) which extend through longitudinally extending spaced-apart parallel slots 136 (see FIG. 14) formed in the upper part or cover 126a. The slots 136 open into four longitudinally extending spaced-apart and parallel recesses 137 (see FIG. 14) formed between downwardly and longitudinally extending ribs 138 formed integral with the upper part or cover 126a. Slide member 141, slide member assemblies 142 and 143 and slide member 144 are slidably mounted in the recesses 137 (see FIG. 14) for movement longitudinally thereof. The slide members 141 and 144 are formed so they are mirror images of each other. Similarly, the slide member assemblies 142 and 143 are also formed so that they are mirror images of each other. Slide members and assemblies 141, 142, 143, and 144 are provided with elongate recesses 146 (see FIG. 14) into which the protruding portions 131b, 132b, 133b, and 134b are snapped and form a friction fit therewith.

The slide members 141 and 144 are provided with tab portions 151 which underlie the intervening rib 138 and extends across the rear or proximal extremity of the slide member assembly 142 or 143 (see FIG. 16). It is also provided with an underlying portion 152 which underlies the slide member assembly 142 or 143 and a depending portion 153. The slide member assembly 142 or 143 consists of a slide member 156 which is provided with an underlying portion 157 at one end which underlies the slide member 141 or 144. Adjoining elongate recesses 158 and 159 are formed in the slide member 156 with recess 158 being deeper than recess 159. Another arcuate recess 161 is formed in the slide member 156 in the bottom of the elongate recess 158 and has disposed therein on opposite ends thereof brake members 162 and 163 formed of a suitable material such as a polycarbonate with a coil spring 166 disposed therebetween. A cover 166 (see FIG. 14) is provided in the elongate recesses 158 and 159 and is slidably movable in recesses 158 and 159 for movement longitudinally of the recesses 158 and 159 by means of two pins 167 fixedly mounted in the slide member 166 on opposite sides of the cover 166 and slidably mounted in the cover 166. The cover 166 is provided with a depending portion 166a (see FIG. 17) which slidably seats in the recess 159 and permitting limited back and forth movement of the cover 166, as for example 0.004" for moving the brake mechanism from a braking position to an unbraked position. Thus, by movement of the cover 166 as hereinafter described, the brake members 162 and 163 can be moved between brake engaging and brake disengaging positions.

The other end of the slide ember 156 is provided with a downwardly extending ledge 168 and a transversely extending insulation stop release arm 169 which is used for a purpose hereinafter described.

A U-shaped clamping member 171 also formed of a suitable polycarbonate material is secured to the upper part or by heat stakes at posts 172 formed integral with the top housing part 126a and underlies the slide members 141 and 144 and the slide member assemblies 142 and 143. The U-shaped frame member 171 is provided with upwardly extending protrusions 173 which are adapted to engage ramp surfaces 174 (see FIG. 17) during actuation of the slide control members 131–134 as hereinafter described.

Means is provided for securing the insulating sleeve assemblies 81 and 82 to the slide control members 141 and 144 and consists of metal tabs 181 soldered to the stainless steel tubes 83 just proximal of the insulation 89. The tabs 181 are secured to the underlying portions 152 of the slide members 141 and 144 by screws 182.

Means is provided for securing the needle electrodes 116 to the slide member assemblies 142 and 143 and consists of metal tabs 186 which are soldered to the electrodes 116 just proximal of the insulation 118. The tabs 186 are secured to the underlying portions 157 of the slide members 156.

Insulated electrical conductors 191 are fastened to the screws 187 so that they are in electrical contact with the tabs 186 and the needle electrodes 116. The conductors 191 extend through a grommet 192 provided in the handle 121 and extend through a cable 193 connected to the handle 121. Similarly the two sets of thermocouple wires 97 extend through the cable 193 and the grommet 192 and into a helically slit protective sleeve 194 and thereafter into a sleeve 196. In the cable 193 the thermocouple wires 97 branch off into another cable 197 (see FIG. 29).

The housing 126 carries a two-part housing extension 198 formed of a polycarbonate which is used for a purpose hereinafter described. It is clapped to the housing 126 by having flange portions 126c and 126d seat in a recess 199 extending around the housing extension 198 (see FIGS. 20–21). The housing extension 198 is provided with a cylindrical extension 201 which can be formed of a suitable material such as a polycarbonate. The cylindrical extension 201 of the housing 126 is adapted to mate with a bridge 206 hereinafter described which is adapted to have mounted thereon the sheath 32 hereinbefore described. The cylindrical extension 201 is provided with a bore 211 (see FIGS. 11 and 23) into which the proximal extremities 57 of the guide tube assemblies 51 and 52 enter and are flared outwardly as shown (see FIG. 3).

Means is provided and connected to the proximal extremities of the guide tube assemblies 51 and 52 for causing actuation of the pull ribbons 76 carried thereby and serves as means carried by the handle means and coupled to the guide tube assembly for causing bending of the distal extremities of the guide tube assemblies 51 and 52 at angles with respect to the longitudinal axes. This means consists of first and second lever assemblies 216 and 217 disposed on opposite sides of the housing 126. Since both the assemblies are the same, only one of them will be described. Lever assembly 216 consists of a cylindrical knob 218 rotatably mounted by a screw 219 to one end of an arm 220. The arm 220 is formed integral with a rotatable member 221 which has a square hole 222 (see FIG. 19) formed therein. A detent and pin disk 223 is rotatably mounted in a cylindrical recess 224 (see FIG. 24) provided in the housing extension 198. The disk 223 is provided with a plurality of circumferentially spaced-apart detents 228 which are adapted to be engaged by plunger 229 which is yieldably urged outwardly by a spring (not shown) loaded into a cylindrical threaded member 231 threaded into a threaded bore 232 provided in the housing extension 198. The disk 226 is provided with a square protrusion 234 which extends through the wall of the housing extension 198 and fits into the square hole 222 of the cylindrical member 221 so that the pin disk 226 can be rotated by movement of the lever arm 220 between two extreme clockwise and counterclockwise positions. The disk 226 is also provided with an upstanding pin 236 which is disposed in a transversely extending slot 237 formed in a rectangular slider block 238 which is slidably mounted for reciprocal movement in an elongate recess 241 overlying the cylindrical recess 227. The slider block 238 is provided with a slot 242 extending longitudinally thereof which is in alignment with an arcuate slot 243 provided in the housing 126 and leading into the bore 202 of the cylindrical extension 201.

The proximal flange 59 of the proximal extremity of the outer guide tube 56 is seated in a slot 240 of the housing extension 198. The actuation or pull ribbon 76 extending proximally of the flange 59 extends into a hole 244 provided in an adjustment block 246 having a leg 247 adapted to move longitudinally in the slot 242. Means is provided for retaining the actuation ribbon 76 within the hole 244 and consists of a tubular member 249 (see FIG. 25) of a suitable material such as stainless steel which can be positioned by a press fit into the hole 244 to retain the proximal extremity of the pull ribbon 76 therein.

Means is provided for providing an adjustment of the pull ribbon with respect to the slider block 238 and consists of a cap screw 251 which is adapted to be threaded into a threaded bore 252 provided in the slider block 238. The adjustment block 246 is provided with slot 254 which is in alignment with the threaded bore 252 and has a transversely extending slot 256 intermediate the ends of the slot 254 which is adapted to receive the head of the cap screw 251. Thus it can be seen by using a conventional screw driver and by adjusting the cap screw 251 it is possible to adjust the longitudinal position of the adjustment block 246 relative to the slider block 238 to thereby adjust the length of the actuation ribbon 76 and the banding which can occur by movement of the lever arm 220 of the lever arm assembly 216 or 217.

In operation, it can be soon that by counterclockwise rotation of the cap screw 251 to in effect loosen the screw will cause the adjustment block 246 to be retracted or to push it away from the slider block 238 and thereby tension the pull ribbon 76. Rotation of the cap screw in the opposite direction causes the opposite to occur. After the appropriate adjustments have been made it can be seen that rotation of the lover arm 220 will cause the pin 236 to slide in the slot 237 to adjust the slider block 238 so that it translates longitudinally of the elongate recess 241 to cause displacement of the ribbon to cause bending of the distal extremity of the associated guide tube assembly as hereinafter described. The spring actuated plunger 229 engaging the detents 228 places a partial restraint on the rotation of the disk 226 and serves to give a physical indication to the physician as the arm 220 is rotated as to the amount of articulation which is occurring, as for example from 0°–30°, from 60°–90°, etc.

The bridge 206 consists of a bridge housing 261 formed (see FIGS. 1, 10 and 11) of a suitable material such as a polycarbonate. A sleeve 263 is mounted therein which can be formed of a suitable material such as stainless steel. The distal extremity of the sleeve is provided with a male threaded extension 264 (see FIG. 1) which is adapted to mate with the locking ring 43 provided on the proximal extremity 33 of the sheath 32. The sleeve 263 is provided with a cylindrical bore (not shown) extending therethrough which is adapted to receive a conventional cystoscope 271. The cystoscope 271 typically is a reusable direct vision device and is provided with a cylindrical stainless steel optical tube 272 which is adapted to fit with a slip fit within the sleeve 263 of the bridge 206. Such an optical tube 272 is well known to those skilled in the art and contains a plurality of rod-like optical elements (not shown) to provide excellent viewing capabilities at the distal extremity 273 of the tube 272. The tube 272 is sized so that it can readily fit within the lumen 36 of the sheath 32 and also so that the distal extremity 273 is disposed immediately to the rear of the curved surface 38 at the distal extremity of the sheath 32 (see FIG. 30). A fitting 274 is provided on the proximal extremity of the tube 272 and carries a port 277 which can be connected a light guide tube 278 connected into a conventional light source 279 (see FIG. 29). An eye piece 281 is carried by the fitting 274.

The bridge 206 is also provided with a downwardly depending bifurcation 286 of two parts 286a and 286b. The bifurcation 286 is provided with a channel 287 for receiving the guide tube assemblies 51 and 52. As can be seen from FIG. 1, the channel 287 is formed in a gradual curve and exits so that it is in alignment with the lower extremity of the lumen 36 provided in the sheath 232 so that the guide tube assemblies 51 and 52 can readily enter the lumen 36 and be advanced to the distal extremity 34 of the sheath 32 as shown in FIG. 30.

Cooperative mating means is carried by the bridge 206 and the handle 121 to prevent deployment of the needle electrodes 116 and the insulating sleeve assemblies 81 and 82 prior to the mating of the handle 121 with the bridge 206. Such means consists of a downwardly extending rail 296 extending longitudinally of the cylindrical extension 201. The rail 296 is rectangular in cross section and has spaced-apart parallel side surfaces 297 and 298. It is also provided with a inclined surface 301 which extends sidewise in proximal direction to the side surface 297 extending from a front surface 302. First and second spaced-apart parallel slots 303 and 304 are provided in the rail 296 and extend upwardly through the side surfaces 297 and 298.

A push button assembly 306 and has a cylindrical plunger body 307 formed of a suitable material such as plastic. It is slidably mounted in spaced-apart aligned holes 308 which open into a well 309. The plunger body 307 is provided with spaced-apart flanges 311 disposed within the well 309. Springs 312 are seated on the plunger body 307 and have one end engaging the flange 311 and the other end engaging the wall forming the well 309. Thus, the springs 312 yieldably retain the plunger body 307 in a midpoint position in the well 309. The plunger body 307 has a central portion 307a which is generally rectangular in cross section and has a width which is slightly less than the width of the slots 303 and 304. The central portion 307a is provided with notches 316 and 317 which are rectangular in cross section and have a height in an axial direction which is slightly greater than the thickness of the rail 296 and which have a depth greater than the depth of the rail 296. The plunger body 307 is also provided with a cylindrical button portions 307b and 307c which extend beyond the sides of the bridge 206 so that they are accessible to the hand of the physician.

Thus, it can be seen that when the guide tube assemblies 51 and 52 are introduced through the bore 288 into the channel 287 and then advanced into the lumen 36 of the sheath 32, the cylindrical extension 201 can be advanced into the bore 288 so that the ramp 301 will cam the push button plunger body 307 sideways so that the notch 317 is urged into registration with the rail 296 against the force of the springs 312. As forward penetration of the cylindrical extension 201 continues, the central portion 307a will come into registration with the first notch 303 and the central body 307a will be returned sideways into engagement with the slot 303 under the force of the springs 312 to arrest further inward movement of the cylindrical extension 201 into the bore 288. Further inward movement of the cylindrical extension 201 into the bore 288 can only occur after the push button plunger body 307 is urged sideways against the yieldable force of the springs 312 so that the notch 317 or 316 is again brought into alignment with the rail 296 after which continued inward movement of the cylindrical extension 201 can be caused to occur until the body portion 307 again moves into the notch 304 under the force of the springs 312.

Latch means is provided to prevent operation of the slide control members 131, 132, 133, and 134 prior to the handle 121 being mated with the bridge 206 as hereinbefore described. Such means consists of a cam release shaft 321 (see FIG. 19) which can be rectangular in cross section which travels in a channel 322 provided in the handle 121. The distal extremity of the cam release shaft 321 is provided with a small plunger 326 which is slidably mounted in a well 327 that is provided in the housing 126.

A first cam member 331 carries pins 332 pivotally mounted in the housing 126 (see FIG. 21). The cam member 331 is provided with a notch 333 which is adapted to be moved into and out of engagement with the slider bar 246. When the slider bar 246 is in engagement with the notch 333 the slider bar 246 cannot move. The cam release shaft 321 and is provided with a pin 336 which is positioned so that it travels in a slot 337 provided in the cam member 331 to actuate the cam member 331. The cam member 331 can therefore be characterized as a front or distal cam member 321 whereas another cam member 341 which is also associated with the cam release shaft 321 can be characterized as a rear or proximal cam release member. The cam release member 341 carries pins 342 pivotally mounted in the housing 126 (see FIG. 22) the cam release member 341 is coupled to the cam release shaft 321 by a pin 343 extending through the cam release shaft 321 travels in a slot 344 in the cam member 341 to drive the cam member 341 into and out of engagement with the U-shaped friction rail 171 to retain the friction rail 171 in a position so that the protrusions 173 carried thereby cannot clear the front surface of the inclined ramp 174 (see FIG. 19) provided on the slide member 142 or 143. The cam member 341 is provided with two paced-apart lobes 341a and 341b (see FIG. 21) which are adapted to engage the two legs of the U-shaped friction rail 171. The proximalmost extremity of the cam release shaft 321 is provided with a shoulder 346 which engages one end of a compression spring 347 which is seated within a well 348 provided in the handle housing 126.

Thus, it can be seen that when the pin 326 is depressed into the well 327 by the cylindrical extension 201 seating in the bore 288 and the bridge 206 engaging the pin 326 against the yieldable force of the spring 347, the front or first cam member 331 is moved so that the notch 334 no longer engages Adjustment block 246 (see FIG. 20) to permit the Adjustment block 246 move. At the same time the second or rear cam release member 341 is moved to the position shown in FIG. 20 to release the friction rail 171 so that the protrusions 172 carried thereby can travel over the ramps 173 to thereby permit movement of the actuation ribbons 76 to permit bending of the distal extremities of the guide tube assemblies 51 and 52 and to permit movement of the slide control members 131–134 as hereinafter described. It should be appreciated that the front and rear cam members 331 and 341 although unitary in construction are provided with lengths which extend across the width of the housing 126 so that both the right and left hand sides of the handle 121 are controlled by the operation of the cams 331 and 341 engaging the corresponding parts on both sides of the handle 121 (see FIGS. 21 and 22) to thereby control both of the guide tube assemblies 51 and 52.

Means is provided for making possible presetting of the amount of extension of the needle electrode 116 in performing ablation procedures hereinafter described and also for preadjusting the distance that the insulating sleeve assemblies 81 and 82 can be withdrawn before starting the application of radio frequency energy in the ablation procedure. Such presetting means consists of a front adjustable push button 351 serving as an insulation stop as hereinafter described and a roar adjustable push button 352 serving as a needle electrode stop as hereinafter described mounted in the housing 126 on each side of the housing (see FIGS. 2 and 13). The push buttons 351 and 352 have stems 353 and 354 which are rectangular in cross section that extend through slots 356 and 357 provided in the sidewall of the housing 126. The stems 353 and 354 are formed integral with the push buttons 351 and 352 and carry rectangular members 366 and 367 which are formed integral therewith and are provided with teeth 368 and 369, respectively, which are adapted to engage teeth 371 and 372 formed on the inner wall forming the housing 126. The teeth 371 and 372 form spaced-apart stationary racks which are adapted to be engaged by the teeth 368 and 369. Suitable means is provided for yieldably urging the members 366 and 367 in a direction towards the outer wall of the housing 126 so that the teeth 368 and 369 carried by the members 366 and 367 are urged into engagement with the teeth 371 and 372 and consist of wall portions 376 and 377 formed integral with the housing 126 and formed of a suitable material such as plastic. This yieldable force can be overcome by pressing inwardly on the knobs or buttons 351 and 352 when it is desired to disengage the teeth 368 and 369 carried by the members 366 and 367 from the teeth 371 and 372 carried by the housing 126.

A latch arm 381 is carried by the somber 366 and is formed integral therewith and is also formed of a suitable material such as plastic. Similarly, a latch arm 382 is mounted on the member 367. The latch arm 381 is provided with an inwardly extending triangular-shaped protrusion 386 which is provided with two adjoining inclined surfaces 388 and 389 inclined in opposite directions. The latch arm 381 is also provided with an inwardly extending protrusion 391 carried on its distal extremity which provides a shoulder 392 facing the surface 389 of the protrusion 386 and an inclined surface 393 facing in a direction away from the shoulder 382 and at an angle with respect thereto.

A latch arm 382 is provided with an inwardly extending protrusion 396 which provides a shoulder 397. The members 366 and 367 in the regions engaging the wall portions 376 and 377 are provided with semi-circular cutouts 378 and 379 to reduce the frictional contact between the members 366 and 367 and the wall portions 376 and 377 during sliding movement of the same in the slots 356 and 357 during positioning of the insulation stop push button 351 and the needle stop push button 352. Scales 398 and 399 for use with the push buttons 351 and 352 can be provided on appropriate surfaces on the housing 126, as for example along the side walls as shown in FIG. 13.

Operation and use of the transurethral needle ablation device 31 in conjunction with performing a procedure on a human male patient suffering from benign prostatic hyperplasia (BPH) may now be briefly described as follows. The male patient 401 to undergo the procedure is partially shown in FIG. 29 in which the anatomy of interest is disclosed and as shown consists of a bladder 402 which is provided with a base or bladder neck 403 which empties into a urethra 404 which can be characterized as being comprised of two portions a prostatic portion 404a and a penile portion 404b. The prostatic portion of 404a is surrounded by the prostate or prostate gland 406 which is a glandular and fibromuscular organ lying immediately below the bladder. The penile portion 404a of the urethra extends through the length of the penis 407. The urethra 404 is formed by a urethral wall 408 which extends through the length of the penis and through the prostate 406 into the bladder 402. The prostate 406 has been characterized as being comprised of five lobes: anterior, posterior, median, right lateral, and left lateral. The prostate 406 is also provided with a verumontanum which is a feature in the prostate to and in positioning the device 31 of the present invention during the procedure hereinafter described.

Let it be assumed that in preparing for the procedure, the prostate of the human male 401 has previously been analyzed to evaluate the size of the prostate by using a digital rectal examination and transrectal ultrasound. In such examination procedures, typically average and peak urine flow, voided volume, residual volume and prostate-specific antigen are measured. Typically the present procedure is most applicable to prostates measuring between 31 as and 64 mm in transverse diameter.

Assuming that the patient's pretreatment evaluation warrants the use of the transurethral needle ablation (TUNA) procedure hereinafter described, the patient 401 can be brought into an outpatient clinic or an operating room in a hospital. The patient is undressed 401 and assumes a reclining position on a procedure or operating table and the legs of the patient are placed in appropriate stirrups to make it possible for the physician to obtain ready access to the pubic region of the patient. A conventional indifferent or grounding electrode 411 (see FIG. 29) is placed on the patient's backside so that it is adherent thereto and sakes good electrical contact with the skin of the patient. The electrode is connected by an electrical cable 412 into a control console and radio frequency generator 413. The control console 413 is provided with an inclined front panel 414 having appropriate digital readouts 415 thereon. A conventional foot operated switch 416 is connected by cable 417 into the control console 413 for controlling the application of radio frequency power as hereinafter described. The handle 121 of the device 31 is connected by the cables 193 and 197 into the control console 413.

Typically the sheath 32 and the bridge 206 as well as the cystoscope 271 forming a part of the device 31 are of the reusable type and would be available in the outpatient clinic or hospital where the patient is to be treated. Only the handle and guide tube assemblies 124 would be considered to be of a disposable type and to be disposed of after a one time use. Thus, upon initiation of the procedure, the handle and guide tube assembly 124 is removed from the sterile packaging as supplied by the manufacturer. The physician knowing the size of the prostate 406 to be treated would make appropriate settings of the front and rear adjustable stop push buttons 351 and 352 provided on opposite sides of the handle housing 126. Thus, the rear adjustable push button 352 would be set in conjunction with a scale 399 provided on the front surface of the handle in accordance with a TUNA treatment table previously generated by the manufacturer to set a needle electrode length ranging from 6–20 mm for a needle electrode 116 having an outside diameter of 0.017" for prostate having a transverse measurement ranging from 31–64 m. The front adjustable insulation stop push button 351 would be set in conjunction with the scale 398 to determine the amount of retraction of the insulating sleeve or shield 81 which for the same size prostate could range from 4–8 mm extending beyond the urethral wall.

In operating the push buttons 351 and 352, they are pushed inwardly against the yieldable force of the wall portions 376 and 377. As soon as a push button 351 or 352 has been pushed in sufficiently far, as for example when the push button 351 is pushed inwardly so that its teeth 368 carried by the member 366 are moved out of engagement with the teeth 371 carried by the housing 126, the insulation stop push button 351 can be moved longitudinally of the housing into the desired position relative to the scale which causes movement of the latch arm 381. As soon as the push button 351 has been advanced to the desired position in accordance with the scale 398, the push button 351 can be released to permit the teeth 368 carried by the member 366 to again re-engage the teeth 371 carried by the wall of the housing 126.

The needle stop push button 352 can be adjusted in a similar manner by pushing inwardly on the button 352 to cause the teeth 369 carried by the member 367 to be moved out of engagement with the teeth 372 on the wall of the housing 126 against the yieldable force of the wall portion 377. As soon as this has been accomplished, the push button 352 can be advanced to the desired position in relationship to the scale 399 carrying with it the latch arm 382.

After the appropriate stop settings have been made by operation of the push buttons 351 and 352, the handle and guide tube assembly 124 can be mated with the bridge 206 by introducing the distal extremities of the guide tube assemblies 51 and 52 through the bridge 206 and through the lumen 36 of the sheath 32. Continued advancement of the guide tube assemblies 51 and 52 brings the cylindrical extension 201 with its rail 296 having the inclined can surface 301 engage the portion 307a of the plunger body 307 to move the plunger body 307 sideways against the force of the springs 312 to bring the notch 317 into registration with the rail 296 to permit the rail 296 to advance further into the bridge 206 until notch 303 is encountered and the springs 312 urge the body 307 in a direction to move the portion 307a into the notch 303 to arrest further inward movement of the cylindrical extension 201 into the bore 288 until after the sheath 32 has been inserted into the urethra 404 as hereinafter described. Assuming that the cystoscope 271 has also been introduced through the bridge 206 and into the sheath 32 so that its distal extremity is also at the distal extremity of the sheath 32, the transurethral needle ablation device 31 is now ready for use.

The physician then introduces a lubricating jelly with a local anesthetic such as Lidocaine into the urethra 404 of the penis 407 utilizing a syringe (not shown) to make it possible for the urethra to accommodate the 22 French size of the sheath 32. In the event the patient has a small urethra, it may be desirable to utilize a series of dilators (not shown) starting with the smallest dilator until the dilator approaching the 22 French in size has been introduced into the urethra. After this has been accomplished, the physician grasps the penis 407 in one hand and utilizes the other hand to grasp the handle 121 of the device 31 and introduces the distal extremity of the sheath 32 into the urethra of the penis and progressively advances the sheath 32 while viewing the advance through the eye piece 281 of the cystoscope 271. During this introduction procedure, the distal extremities or tips of the guide tube assemblies 51 and 52 are immediately proximal of the curved surface 38 of the sheath 32 so that the urethral wall is protected from the distal extremities of the guide tube assemblies 51 and 52 which carry the needle electrodes 116 that extend a short distance, as for example 1–2 m from the distal extremity of the insulating tubes 86. In other words, the tips or distal extremities of the guide tube assemblies 51 and 52 are hidden under the distal extremity of the sheath 32. Also advantageous is that the distal extremities of the guide tube assemblies 51 and 52 will not interfere with the physician's vision through the cystoscope 271 making it possible for the physician to identify physiological features inside of the urethra, as for example the verumontanum in the prostate and the sphincter prior to the bladder during advancement of the sheath 32. Utilizing these parts of the sale anatomy, the physician is able to properly identify the location in the prostate of which he wishes to perform the ablation procedure and rotates the handle 121 so that the needle electrodes 116 to be deployed will enter the appropriate lobe of the prostate.

As soon as the sheath 32 is in the proper position within the prostate 406, as for example in the position shown in FIG. 29, the physician operates the push button plunger 307 by pushing inwardly on either the left, side button portion 307b or the right side button portion 307a to urge the plunger body 307 bin the desired direction against the force of the springs 312 to move one of the notches 316 or 317 into registration with the rail 296 to permit further insertion of the cylindrical extension 201 into the bore 288 so that the bridge 206 engages the pin 326 to move the cam release shaft 321 downwardly and rearwardly against the force of the spring 347 to operate the cam members 331 and 341. The distal extremities of the guide tube assemblies 51 and 52 will be deployed or positioned distally of the distal extremity of the sheath 31 ready to be bent.

It can be seen that the two steps required for complete mating of the cylindrical extension 201 in the bore 288 of the bridge 206 by the use of the two notches 303 and 304 provides a safety feature in that it prevents untimely deployment and bending of the distal extremities of the guide tube assemblies 51 and 52 the needle electrodes 116 which could damage the urethral wall 408 during insertion of the sheath 32.

As soon as the distal extremities of the guide tube assemblies 51 and 52 extend beyond the distal extremity of the sheath 32, the distal extremities of the guide tube assemblies 51 and 52 can be bent so that they extend at an angle of preferably 90° with respect to longitudinal axis of the guide tube assemblies 51 and 52 as shown in FIG. 30 and so that needle electrodes 116 carried thereby extend in a direction which is generally perpendicular to the urethral wall 408 of the prostate This is accomplished by moving the lever assemblies 216 and 217 forwardly by pushing on the knobs 218. The positioning of the distal extremities of the guide tube assemblies 51 and 52 can be visually observed by the physician through the cystoscope 271 while pushing on the knobs 218. Because of the slotted construction of the distal extremities of the guide tube assemblies 51 and 52 as hereinbefore described, the prehensile guide tube assemblies 51 and 52 can be bent through the 90° desired angle in a small diameter, as for example 5–10 m or less and still readily clear the distal extremity of the sheath 32. Typically, the bent distal extremities of the guide tube assemblies 51 and 52 are disposed at a certain angle with respect to each other in generally the same plane, as for example an angle ranging from 30–75° and preferably an angle of approximately 60°.

The slide control embers 131–134 can be advanced as two different sets with one set being the control members 131 and 132 and the other set being the control members 133 and 134. An hereinbefore explained, the slide control members 132 and 133 control the deployment of the needle electrodes 116. Movement of the slide control members 132 and 133 in a forward direction at the same time also causes simultaneous movement of the slide control members 131 and 134 which control the deployment of the insulation tubes 86 so that deployment of the needle electrodes 116 causes the insulating tubes 86 to be advanced simultaneously with the relative positioning between a needle electrode 116 and the insulation tube 86 surrounding the same being such that the needle electrode only protrudes a very -small distance, as for example 1–2 mm beyond the distal extremity of the insulation tube 86. This simultaneous movement is caused because the slide control member 131 causes movement of the slide member 141 which has a tab portion 151 carried thereby which extends across rear of the slide member 142. Thus, during the advancement of the slide control members 131 and 132, the needle electrode 116 is caused to penetrate the urethral wall 408 (see FIG. 32)

closely followed by the insulating tube 86. Penetration of the urethral wall 408 in this manner causes tenting of the urethral wall as shown in FIG. 32 which tenting continues as the needle 116 and insulating tube 86 are advanced into the tissue of the prostate 406. The advancement continues until the slide control member 132 and the slide control member 133 reach their appropriate stops provided by the front adjustable push buttons 352. This determines the maximum penetration for the needle electrode 116 into the prostate as hereinbefore determined in accordance with the settings for the push buttons 352. This needle stop is provided by the structure shown in FIG. 26 in which the shoulders 397 provided on the protrusions 396 of the latch arms 382 are engaged by a surface of the portion 157 of the needle electrode slide member 156. In the advancement of the insulation slide members 141 and 144, the slide members can be readily pushed over the extremity of the latch arm 381 by the portions 153 engaging the cam surfaces 393 to cam the arms 381 out of the way and to permit the portions 153 to seat within the space provided between the shoulders 392 and the inclined surfaces 389 provided on the protrusions 386.

An soon as the slide control members 131–134 have been advanced to their forwardmost positions as determined by the push buttons 351, the slide control members 131 and 134 are retracted to cause withdrawing of the insulation tubes 86. This retraction of the slide control members 131 and 134 is continued until they reach their rearmost extremity as determined by the front push buttons 351. Rearward movement of the insulation slides 141 and 144 is arrested by the portions 153 of the insulation slide members 141 and 144 coming into engagement with the shoulders 392 carried by the latch arms 381. As the insulation tubes 86 are withdrawn, the tenting which had previously occurred in the urethral wall 408 is eliminated by the pulling back of the insulation tubes 86 the needle electrodes 116 remain in their desired extended positions. However, as hereinafter explained, the insulation sheaths or tubes 86 are only retracted sufficiently so that there still remains insulation tube 86 extending through the urethral wall 408 to protect the urethral wall 408 as hereinafter described. During this retraction of the insulation tubes 86, the slide control members 132 and 133 have a tendency to move therewith because of frictional contact with adjacent slide members 131 and 134. However, movement of slide member assemblies 142 and 143 in a rearward direction from the forwardmost extremity hereinbefore determined by the front adjustable push button 351 will not occur because the slide members 156 are frictionally retained by the braking provided by the brake members 162 and 163 yieldably and frictionally engaging the associated rib 138.

After these procedures have been accomplished, the patient 401 is ready to have radio frequency energy supplied to the needle electrodes 116 which are in the desired appropriate positions within the tissue of the appropriate lobe of the prostate 406. Radio frequency energy is supplied from the control console and radio frequency generator 413 (see FIG. 29) by operation of the foot switch 416 by the physician. This causes radio frequency energy of the desired frequency and power level (preset by the physician) to be supplied to the needle electrodes 116 disposed within the prostatic tissue 406.

It has been found that in order to optimize the performance of the needle electrodes 116 it is desirable to supply radio frequency energy to the two electrodes 116 at two different radio frequencies with frequencies which are not a harmonic of the other. Typically, the radio frequencies can range from 300 kHz to 1 mHz although frequencies ranging from 250 kHz to 20 mHz can be utilized if desired. By way of example, it was found that variable desirable performance can be achieved by supplying a radio frequency energy of 460.8 kHz to one electrode and 482.4 kHz to the other electrode.

The radio frequency energy is delivered at power levels which can range from 2–9 watts with the surface area of the needle ranging from 0–30 square millimeters. Thus, by way of example, a needle electrode having a diameter of 0.017" and having an exposed length ranging from 6–22 mm can have a surface area ranging from 3–26 square millimeters. The time of application of radio frequency energy can range from 2–15 min., however, typically it has been found that a period of 4–5 min. is appropriate. By way of example, initial power could be delivered at 4 watts for 1 min. and thereafter adjusted to 5 watts for the second minute and then adjusted to 6 watts for the 3rd, 4th, and 5th minutes of radio frequency energy application.

A slow and steady rising shield temperature, i.e. 5–8° C. typically is observed during the course of a treatment. If the temperature rises less than 5° C. per minute, the radio frequency power is increased by approximately 1 watt. Conversely, if the temperature rises greater than 8° C. per minute, or if there is a sudden increase in impedance, the radio frequency power applied is decreased by approximately 1 watt.

The retractable shield 86 provided on the needle electrode 116 serves to protect the urethral wall 408 from damage from the radio frequency energy. The thermocouples provided at the ends of the insulating sleeve assemblies 81 and 82 monitor the temperature of the prostatic urethral wall 408. In addition, the same thermocouples monitor the prostatic temperature proximal to lesions which are created by the needle electrodes. These lesions are created by conduction of radio frequency energy from the outer surface area of the needle electrode 116 exposed in the tissue of the prostate and passing through the tissue thence into the body of the patient to the indifferent electrode 411 and then back to the RF power supply 413 to complete the electrical circuit for the radio frequency energy. A lesion 429 is formed about each of the electrodes 116 with the urethral wall 408 being protected from the heat generated by the insulating tube 86.

The formation of lesions around the needle electrodes 116 by the radio frequency energy applied from the needle electrodes can be explained because body tissue are mainly electrolytes, fat and calcium and interact with electromagnetic radiation differently at different wavelength. Since the tissues are fairly uniformly permeated by a saline solution with constant concentration of electrolytes, the tissue will behave as a poor conductor. If the wavelength of the electric field applied to body tissues is long relative to the human body dimensions (at 500 kHz it is 600 meters), the interaction will be mainly losses in moving ions and water molecules at the frequency of the electric heat. The higher the current, the more vigorous the motion of the molecules and the higher the temperature reached over a given time. If the field is applied between two equal size electrodes, the current flow per unit area of the electrode, defined as current density, will be similar at both electrodes. If one electrode is much smaller, the total amount of current still has to flow and the current density will be such higher, with corresponding higher temperatures at the small electrode, as for example at the needle electrodes. If the tissue is heated to the point of desiccation, there is no more conduction present, the tissue becomes a dielectric and current as well as heating stops. This shows up an a significant increase of tissue resistance. Representative results from the application of radio frequency energy utilizing devices such as device 31 of the present invention resulted in the creation of localized lesions averaging 12×7 mm with larger lesions being formed when desired showing extensive coagulative and necrosis averaging 30×15 mm. 4 to 15 watts of power were applied for approximately 3 min.

A representative thermal gradient map is shown in FIG. 34 in which isothermal lines 431 represent the different temperatures believed to be encountered in the prostatic tissue 406 during creation of a lesion with a device 31. It can be seen that from FIG. 34 that the isothermal lines form generally ovoid envelopes extending around and forwardly of the needle electrode 116 in a direction toward the return electrode 411 starting with a temperature of 100° C. in close proximity to the electrode 116. The isothermal lines 431 show that the temperature in the prostatic tissue drops off in a progressive fashion through isothermal gradient lines of 90° C., 80° C., and 60° C. representing generally the total volume of the necrosis occurring in the prostatic tissue to form a lesion. Typically, the average gradient from the surface of the needle electrode 116 to the periphery of the lesion created was approximately 50° C. per millimeter with an average maximum temperature of approximately 100° C. As it is well known to those skilled in the art, at temperatures below approximately 55° C., there is no deleterious degradation of the prostatic tissue.

By viewing the isothermal gradient lines 431 in FIG. 34, it can be seen that it is possible to relatively precisely control the size of the lesions created by carefully monitoring the temperatures reached in the prostatic tissue. In the present application, this is done by the thermocouples 96 placed at the distal extremities of the insulating sleeve assemblies 81 and 82. It should be appreciated that if desired additional thermal measurements can be made, as for example by the use of a rectal probe placed in close proximity to the prostate to ensure that undue heating does not occur. It should be appreciated that the radio frequency generator 413 is provided with controls which will automatically shut off the application of RF power in the event excessive temperatures are sensed by the thermocouples.

It was found that there was a direct relationship between the amount of surface area exposed on the needle and the amount of energy applied and the time it is applied. Thus, by way of example small lesions can be created of 2–4 mm by the application of power of approximately 2–3 watts substantially independent of the millimeters of needle electrode exposure. However, with the application of increased power, as for example from 3–8 watts for a period of 1 min. medium size lesions ranging from 4–7 mm in width could be obtained with needle exposures ranging from 5–10 mm. Still larger but still medium size lesions ranging from 4–8 mm in width could be obtained with the application of radio frequency power from 3–12 watts for periods of time ranging from 2–4 min. with 10 mm and greater of electrode needle exposure. Large lesions ranging from 8–10 mm in width could be obtained by the application of power from approximately 5–15 watts of radio frequency energy for a period of time ranging from 3–5 min. with needle electrode exposures of 15 mm and greater. Very large lesions, as for example those greater than 10 mm in width may be achieved by the application of power ranging from 5–15 watts for periods of time in excess of 4 min. with needle exposures greater than 15 mm.

Thus, utilizing the procedure hereinbefore described, for more specific results, the two needle electrodes 116 which are disposed at an acute angle of 60° were introduced into one of the lateral lobes of the prostate. With the application of 4–15 watts of radio frequency energy applied for a period of 3 min. the proximal lesion temperature was approximately 40–500° C. with the central lesion temperature of approximately 80–100° C. The temperature at the urethral wall 408 averaged 37–42° C. which is well below the 55° C. at which thermal damage of the urethral wall 408 could occur. By the controlled application of radio frequency energy over predetermined time, it is possible with the present procedure to preserve the urethral wall and also to preserve the integrity of the capsule surrounding the prostate. In other words, the lesions were created well within the lateral lobe and spaced from the urethral wall and from the prostatic capsule.

After one of the lateral lobes of the prostate 406 has been treated by the formation of two lesions by the two needle electrodes 116, the physician while using the cystoscope 271 pulls back on the slide control members 132 and 133 controlling the deployment of the needle electrodes 116. This pulling back of the slide control members 132 and 133 moves the slide member assemblies 142 and 143 rearwardly which overcomes the brake action of the brake members 162 and 163 so that the slide member assemblies 142 and 143 come into engagement with the tab portions 151 to also cause retraction of the slide control members 131 and 134.

The rearward movement of the slide member assemblies 142 and 143 and carrying the needle electrodes 116 and carrying with them the insulation slide members is made possible by the insulation slide members 141 and 144 being freed from the latch arms 381 by having the insulation stop release arm 169 carried by the needle electrode slide member assemblies 142 and 143 engaging the can surfaces 388 provided by their protrusions 386 to cam the latch arm 381 outwardly towards the side wall of the housing 126 to release the portion 153 carried by the insulation slide members 141 and 144 (see FIG. 26) and to thereafter permit continued rearward movement of slide ember assemblies 142 and 143 and carrying with them the slide members 141 and 144 until a rearmost position is reached. The guide tube assemblies 51 and 52 can then be straightened by pulling back on the lever assemblies 216 and 217.

Assuming that the needle electrodes 116 were introduced into one of the lateral lobes of the prostate 406 in a plane, as for example a plane just below the bladder neck, the sheath 32 can be retracted with the needle electrodes 116 and the insulation tubes 86 so that they are withdrawn behind the urethral wall 408. The sheath 32 then can be rotated, as for example by 120° so that the distal extremities of the electrodes 116 remain in the same plane but are opposite the other lateral lobe of the prostate. As soon as this repositioning has been accomplished, the lever assemblies 216 and 217 can be operated to again bend the distal extremities of the guide tube assemblies 51 and 52 in the manner hereinbefore described. Thereafter the slide control members 131–134 can be actuated in the manner hereinbefore described to cause the needle electrodes 116 and the insulation sheaths 86 to penetrate the urethral wall 408 and to advance into the prostatic tissue in the other lateral lobe. Assuming that the same presettings utilized for the other lateral lobe are used, the needle electrode 116 is extended into the desired position into the tissue of the other lateral lobe and the appropriate length of needle electrode exposed by withdrawing the insulator tube 86 so that it exposes the needle electrode 116 but still is disposed a distance beyond the urethral wall 408 so that the urethral wall 408 is protected during the procedure. Thereafter, radio frequency energy is again applied at the appropriate power level and time to create two lesions in the other lateral lobe. After this has been accomplished, the needle electrodes 116 and the insulation tubes 86 can be withdrawn as hereinbefore described so that they are retracted behind the urethral wall 408. Thereafter, if additional lesions are desired in the prostate 406 in different planes, the distal extremity of the sheath 32 is repositioned by the physician grasping the handle 121 to an inferior plane with the same procedure being repeated for both lateral lobes in the next inferior plane.

It has been found that the number of treatment planes or planes in which the lesions are to be created depends upon the size of the prostate being treated. Thus, where the distance from the verumontanum to the bladder neck is less than 3 cm, a single treatment plane normally is only necessary and this treatment plane is at the midpoint between the verumontanum and the bladder neck. If the distance from the verumontanum to the bladder neck is in excess of 3 cm to 4 cm two treatment planes are generally utilized with the proximal plane being approximately 2 cm from the verumontanum and the other treatment plane being approximately 1 cm to the verumontanum. The distance from the verumontanum to the bladder neck is greater than 4 cm typically three transverse treatment planes are provided anteriorly at 1, 2 and 3 cm from the verumontanum.

After the desired number of lesions have been formed in the prostatic tissue 406, the slide control members 131–134 can be brought to the rear after which the knobs 218 controlling the lever assemblies 216 and 217 can be pulled rearwardly to remove the 90° bends in the distal extremities of the guide tube assemblies 51 and 52. The distal extremities of the guide tube assemblies 51 and 52 are retracted to within the distal extremity of the sheath 32 by pushing on the push button 307b or 307c to bring one of the notches 316 or 317 into alignment with the rail 296 to permit partial retraction of the handle and guide tube assembly 124 so that the distal extremities of the guide tube assemblies 51 and 52 are retracted into the sheath. As soon as this has been accomplished, the entire transurethral needle ablation device 31 can be removed from the urethra 404 of the penis 407 to complete the TUNA procedure.

At this point, the physician may choose to introduce an antibiotic into the urethra 404 to help prevent an infection from occurring. With the procedure completed, the patient typically can rest for a short period of time and then can leave the procedure room and go to his home.

In the TUNA procedure, the distal extremity of the needle electrode was always positioned so that it was at least 6 mm from the capsule of the prostate to ensure that the integrity of the capsule would not be impaired by the TUNA procedure. Similarly, the insulation tube 86 was deployed beyond the urethra wall for a distance ranging from 4–6 mm to also ensure the integrity of the urethral wall is not impaired by the TUNA procedure. The small hole or holes which are punched through the urethral wall readily heal after the TUNA procedure.

Typically, a patient who has undergone the TUNA procedure and prior thereto had difficulty in urinating will after the procedure experience some smooth muscle tissue relaxation which results in a reduced constriction of the urethra. Thus in a very short term ranging from a few hours to 24–48 hours, the patient experiences none degree of improvement in urinary flow. Over the longer term, it has been found that catheterization is unnecessary and that the patient experiences improved urinary flow within a relatively short period of time ranging from 1–4 days. Longer term results of patients undergoing the TUNA procedure have shown that after 6–12 weeks, the patients have vastly improved urinary flows and that even after 6–9 months following the TUNA procedure, the patients experience urinary flows which are equivalent to that of a young male.

In connection with the present TUNA procedure it has been found that to create an irreversible tissue lesion in the prostatic tissue to provide the lasting clinical benefits hereinbefore described, temperatures above 45° C. can cause some cellular necrosis if that temperature is applied for a significant period of time. However, to achieve thermal ablation in connection with the present TUNA procedure, it is desirable to provide temperatures of 60° C. and greater so as to shorten the time of application of radio frequency energy to reasonable periods of time. Thus, even when multiple lesions are created in the prostatic tissue, the entire procedure typically can be accomplished in 15–25 min. with the use of the TUNA device 31. High temperatures substantially in excess of 60° C. are readily achieved ranging from 80–100° C. localized around the needle electrode 116 and need be applied for only 3–5 min. Thus, although the temperature measured at the tip of the insulation tube 86 can be as high as 75° C., the temperature at the tip of the needle electrode is typically 30–45° C. higher. As hereinbefore explained major necrotic lesions can be obtained with the lesions exhibiting extensive coagulative necrosis measuring 15×8 mm macroscopically and 30×15 mm microscopically at approximately 30 days after the TUNA procedure. The penetration of electromagnetic waves into the tissue of the prostate depends upon their frequency. With the lower the frequency the higher the penetration. The radio frequency energy is utilized in connection with the TUNA device 31 utilizes radio frequency in the vicinity of 490 kHz which provides a deeper penetration and more uniform temperature distribution of then microwaves at 300–3000 kHz. The TUNA device makes it possible to create lesions with sharply defined margins using very low power levels, i.e. 5–10 watts. This is due to a steep temperature gradient from the needle to the periphery of the lesion. This is in comparison to transurethral microwave therapy which produces a temperature gradient of 5–15° C. over a few millimeters in the lesion area adjacent to the urethra and 1–2° C. per millimeter near the capsule. The TUNA device on the other hand utilizes the radio frequency energy in the vicinity of the 490 kHz makes it possible to provide a much steeper gradient near the proximal end of the needle electrode 116 of 58° C. per millimeter (the area near the urethral wall) near the needle tip of 30° C. per millimeter (the area near the prostatic capsule).

From the foregoing it can be seen that the TUNA procedure utilizing the TUNA device of the present invention makes it possible to provide very selective controlled localized ablation areas in the prostate. The integrity of the prostatic capsule and the urethral wall is maintained. The urethral wall recovers rapidly from the minor punctures which occur in the urethral wall during the procedure. Bleeding is minimized and the potential for infection is greatly decreased. Although as many as eight to 12 lesions may be required in any one prostate, the procedure still can be accomplished in a period of time ranging from 20–40 min. The procedure can be accomplished relatively inexpensively in an outpatient environment with only a local anesthetic being required. Thus, it can be seen that the TUNA procedure provides a viable inexpensive alternative to conventional procedures heretofore utilized for treating benign prostatic hyperplasia.

Another embodiment of a TUNA device which can be characterized as the TUNA IV is shown in FIGS. 35–38 and identified as device 451 therein. It consists of a handle and guide tube assembly 452 which is very similar to the handle and guide tube assembly 124 hereinbefore described in conjunction with TUNA III. The handle and guide tube assembly 452 is adapted to mate with a bridge 456 which is also of the type hereinbefore described for TUNA III. A sheath 461 is coupled to the bridge 456 in the same manner as the sheath 32. However, the sheath 461 is of a smaller size, as for example a 16 French rather than the 22 French for the sheath 32 to make it possible to enter the urethra of the penis without requiring the substantial additional enlargement required by the sheath 32. The sheath 461 has a lumen 462 in which a fiber optic tube 466 of smaller diameter than the tube 272 is disposed in association with guide tube assemblies 51 and 52 to provide a generally triangular configuration as shown in FIG. 37. The fiber optic tube 466 has an outer stainless steel tube 468 having an outside diameter of 0.05", an inner sheath 469 of polyimide is provided in tube 468 and incases a hollow cylindrical light fiber bundle 471. The bundle 471 encases a viewing fiber bundle 472. A lens assembly 476 consisting of a cylindrical lens cell 477 with internal steps carries a plano-convex lens 478 at each end. The lens cell 477 has one end abutting the distal extremity of the viewing fiber bundle 472 in a butt joint 481 formed by an ultraviolet cured adhesive. The lens cell 477 is supported within the distal extremity of the light fiber bundle 471 which is supported by inner and outer polyimide sheaths 483 and 484 secured by adhesive in a butt joint 486 to take 468 and the polyimide sheath 469. The lens cell 477 with its plano-convex lenses 478 provides a wider field of vision.

The sheath 461 rather than being formed of stainless steel also can be formed of plastic but typically the thin all stainless tube is more appropriate to obtain the desired rigidity to facilitate the introduction of the TUNA IV device into the urethra to lift and straighten out the urethra while introducing the sheath into the prostate.

The fiber optic tube 466 forms a part of a cystoscope 491 which is provided with an eye piece 492. The cystoscope 491 extends through a tricoupler 496 which is mounted on the proximal extremity of the bridge 456. The tricoupler 496 is provided with first and second ports 497 and 498 in which port 497 can be utilized for introducing light whereas the other port 498 can be utilized for introducing a fluid.

An adjustment mechanism 501 is provided on the cystoscope 491 to permit adjustment of the cystoscope longitudinally of the bridge 456 so that the plano convex lenses 478 can be appropriately positioned with respect to the distal extremity of the sheath 461. This adjustment means consists of a threaded cap 502 threaded onto an extension 503 of the tricoupler body 504. An optical coupler 506 is slidably mounted in a well 507 provided in the body and has a radially extending flange 508 underlying the cap 502. The optical coupler 506 extends through a hole 509 in the cap 502 and has a threaded portion 506a onto which a nut 511 is threaded to retain the coupler 506 on the cap 502. The fiber optic tube 466 is connected to the coupler 506 and moves with the coupler 506. The coupler 506 carries the viewing fibers 472 and the light transmitting fibers 471. It can be seen that as the cap screw 502 is adjusted longitudinally of the body 504, it will carry with it the fiber optic tube 466 so that the distal extremity carrying the plano-convex lens 478 can be precisely adjusted with respect to the distal extremity of the sheath 461 to optimize the viewing capabilities of the device 451.

The TUNA IV device 451 can be utilized in the same manner as the TUNA III device 31 in performing a TUNA procedure hereinbefore described. The principal advantage of the TUNA IV device is that it can be utilized in males having smaller urethras or alternatively can be utilized in males without requiring extensive distention of the urethral wall of the patient. It also is provided with adjustment means to optimize the optical viewing.

What is claimed is:

1. A medical device for the treatment by radio frequency ablation of a target volume in tissue of a prostate of a human having a urethral channel extending into a base of a bladder along a longitudinal axis comprising an elongate probe member having proximal and distal extremities, the elongate probe member having an opening in the distal extremity and a passage therein extending from the proximal extremity to the opening in the distal extremity, the elongate probe member being sized so that it can be introduced into the urethra, guide means having proximal and distal extremities, means for removably mounting the proximal extremity of the guide means to the proximal extremity of the elongate probe member so that the guide means extends through the passage of the elongate probe member and the distal extremity of the guide means is in vicinity of the opening in the distal extremity of the elongate probe member, the guide means having a lumen extending therethrough from the proximal extremity to the distal extremity, a radio frequency conductive electrode slidably disposed in the lumen, handle means coupled to the proximal extremity of the elongate probe member, the handle means including finger actuatable means secured to the radio frequency electrode for advancing and retracting the radio frequency electrode with respect to the guide means, the distal extremity of the guide means having a curved surface disposed outside the opening for directing the radio frequency electrode sidewise of the longitudinal axis into the tissue of the prostate.

2. A device as in claim 1 wherein the handle means includes means secured to the proximal extremity of the guide means for selectively bending the distal extremity of the guide means to thereby control the direction of penetration of the radio frequency electrode into the tissue.

3. A device as in claim 1 wherein the distal extremity of the guide means is movable from a substantially straightened position to a bent position for forming the curved surface.

4. A device as in claim 2 wherein the distal extremity of the guide means is provided with a plurality of longitudinally spaced-apart slots for facilitating bending of the distal extremity of the guide means.

5. A medical device for treatment by radio frequency ablation of a target volume in tissue of a human having a urethral channel extending into the base of a bladder along a longitudinal axis comprising an elongate probe member having proximal and distal extremities, the elongate probe member having an opening in the distal extremity and a passage extending from the proximal extremity to the opening in the distal extremity, the elongate probe member being sized so that it can be introduced into the urethra, elongate guide means having proximal and distal extremities, means for removably mounting the proximal extremity of the elongate guide means to the proximal extremity of the elongate probe member so that the elongate guide means extends through the passage of the elongate probe member with the distal extremity of the elongate guide means being in the vicinity of the opening in the distal extremity of the elongate probe member, the elongate guide means having at least first and second lumens extending therethrough from the proximal extremity to the distal extremity, a radio frequency conductive electrode slidably disposed in each lumen, handle means coupled to the proximal extremity of the elongate probe member, the handle means including hand operable means secured to the radio frequency electrodes for advancing and retracting each of the radio frequency electrodes with respect to the elongate guide means and the tissue of the target volume.

6. A device as in claim 5 wherein the distal extremity of the elongate guide means has a curvature for directing the radio frequency electrodes sidewise of the longitudinal axis.

7. A device as in claim 6 wherein the distal extremity of the elongate guide means is movable from a substantially straightened position to a bent position for forming the curvature.

8. A device as in claim 5 wherein the handle means includes means for selectively bending the distal extremity of the elongate guide means to control the direction of penetration of the radio frequency electrodes into the tissue of the target volume.

9. A medical device for the treatment by radio frequency ablation of a target volume in tissue of a prostate of a human male having a bladder with a base and a penis with a urethra therein formed by a urethral wall extending into the base of the bladder along a longitudinal axis with the tissue of the prostate surrounding the urethra near the base of the bladder comprising an elongate probe member having proximal and distal extremities, the elongate probe member having an opening in the distal extremity and a passage therein extending from the proximal extremity to the opening in the distal extremity, the elongate probe member being sized so that it can be introduced into the urethra, a plurality of guide tubes having proximal and distal extremities with portions between the proximal and distal extremities, means for removably mounting the proximal extremities of the guide tubes to the proximal extremity of the elongate probe member so that the guide tubes extend through the passage of the elongate probe member and the distal extremity of the guide tubes are in the vicinity of the opening in the distal extremity of the elongate probe member, means for fastening together said portions of the guide tubes, each of the guide tubes having a lumen extending therethrough from the proximal extremity to the distal extremity, a radio frequency conductive electrode slidably disposed in each lumen, handle means coupled to the proximal extremity of the elongate probe member and including hand operable means secured to the radio frequency electrode in each lumen whereby the radio frequency electrode in each lumen can be advanced and retracted with respect to the guide tube and the tissue of the prostate.

10. A device as in claim 9 wherein the handle means includes means for selectively bending the distal extremity of each of the guide tubes to control the direction of penetration of the respective radio frequency conductive electrode into the tissue of the prostate.

11. A device as in claim 9 wherein the distal extremity of each of the guide tubes has a curvature for directing the respective radio frequency conductive electrode sidewise of the longitudinal axis.

12. A device as in claim 11 wherein the distal extremity of each of the guide tubes is movable from a substantially straightened position to a bent position for forming the curvature.

13. A medical device for use with an elongate probe member to treat by radio frequency ablation a target volume in tissue of a prostate of a human having a urethral channel extending into the base of a bladder along a longitudinal axis, the elongate probe member having proximal and distal extremities and being sized so that it can be introduced into the urethra, the elongate probe member having an opening in the distal extremity and a passage extending from the proximal extremity to the opening in the distal extremity, comprising a guide member having proximal and distal extremities, means adapted for removably mounting the proximal extremity of the guide member to the proximal extremity of the elongate probe member so that the distal extremity of the guide member is in the vicinity of the opening in the distal extremity of the elongate probe member, the guide member having a lumen extending therethrough from the proximal extremity to the distal extremity, a radio frequency conductive electrode slidably disposed in the lumen of the guide member, handle means coupled to the proximal extremity of the guide member and including hand operable means secured to the radio frequency electrode for advancing and retracting the radio frequency electrode with respect to the guide member, the distal extremity of the guide member having a curved surface for disposition outside of the opening to direct the radio frequency electrode sidewise of the longitudinal axis into the tissue of the prostate.

14. A device as in claim 13 wherein the distal extremity of the guide member is movable from a substantially straightened position to a bent position for forming the curved surface.

15. A device as in claim 13 wherein the handle means includes means secured to the proximal extremity of the guide member for selectively bending the distal extremity of the guide member to thereby control the direction of penetration of the radio frequency electrode into the tissue of the prostate.

\* \* \* \* \*